(12) United States Patent
Uhlmann et al.

(10) Patent No.: US 6,905,820 B2
(45) Date of Patent: Jun. 14, 2005

(54) POLYAMIDE NUCLEIC ACID DERIVATIVES, AND AGENTS AND PROCESSES FOR PREPARING THEM

(75) Inventors: Eugen Uhlmann, Glashütten (DE); Gerhard Breipohl, Frankfurt (DE); David William Will, Kriftel (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 359 days.

(21) Appl. No.: 09/835,371

(22) Filed: Apr. 17, 2001

(65) Prior Publication Data

US 2002/0187473 A1 Dec. 12, 2002

(30) Foreign Application Priority Data

Apr. 18, 2000 (DE) .......................................... 100 19 135

(51) Int. Cl.[7] .......................... C12Q 1/68; C12P 19/34; C12M 1/34; C07H 21/02; C07H 21/64

(52) U.S. Cl. .......................... 435/6; 435/7.1; 435/91.1; 435/91.2; 435/287.2; 536/22.1; 536/23.2; 536/24.3; 536/24.31; 536/24.32; 536/24.33; 530/322

(58) Field of Search ........................... 435/6, 7.1, 91.1, 435/91.2, 287.2; 536/22.1, 23.1, 24.3–33; 530/322

(56) References Cited

U.S. PATENT DOCUMENTS

| | | | |
|---|---|---|---|
| 5,874,553 A | | 2/1999 | Peyman et al. |
| 6,043,352 A | * | 3/2000 | Manoharan et al. ....... 536/24.2 |
| 6,046,306 A | * | 4/2000 | Breipohl et al. ............ 530/322 |

FOREIGN PATENT DOCUMENTS

| | | |
|---|---|---|
| CA | 2144475 | 9/1995 |
| CA | 2217377 | 4/1998 |
| DE | 195 08 923 | 9/1996 |
| DE | 196 40 974 | 4/1998 |
| EP | 0 672 677 | 9/1995 |
| WO | WO 92/20702 | 11/1992 |
| WO | WO 96/11205 | 4/1996 |
| WO | WO 99/33867 | 7/1999 |
| WO | WO 99/37670 | 7/1999 |

OTHER PUBLICATIONS

Uhlmann et al Nucleosides & Nucleotides vol. 16 (5&6) pp. 603–608 1997.*
Weiler et al (NAR vol. 25 No. 14 pp. 2792–2799 1997.*
Nielsen et al., "Sequence–Selective Recognition of DNA of Strand Displacement with a Thymine–Substituted Polyamide", Science 254:1497–1500, Dec. 6, 1991.
Egholm et al., "PNA Hybridizes to Complementary Oligonucleotides Obeying the Watson–Crick Hydrogen–Bonding Rules", Nature 365(6446):566–568, Oct. 7, 1993.

(Continued)

Primary Examiner—Jeffrey Siew
(74) Attorney, Agent, or Firm—F. Aarim Dubberly

(57) ABSTRACT

The present invention relates to PNA derivatives which carry, at the C terminus, or at both the C and N termini of the PNA backbone, one or more phosphoryl radicals. The phosphoryl radicals carry, where appropriate, one or more labeling groups, groups for crosslinking, groups which promote intracellular uptake, or groups which increase the binding affinity of the PNA derivative for nucleic acids. The invention furthermore relates to a process for preparing the above-mentioned PNA derivatives and to their use as pharmaceuticals or diagnostic agents.

69 Claims, 16 Drawing Sheets

OTHER PUBLICATIONS

Nielsen et al., "Peptide Nucleic Acid (PNA). A DNA Mimic with a Peptide Backbone", *Bioconjugate Chem.* 5(1):3–7, Jan./Feb. 1994.

Uhlmann et al., "PNA: Synthetic Polyamide Nucleic Acids with Unusual Binding Properties", *Angew. Chem. Int. Ed.* 37(20):2796–2823, Nov. 2, 1998.

Greiner et al., "Influence of the Type of Junction in DNA–3'–Peptide Nucleic Acid (PNA) Chimeras on Their Binding Affinity to DNA and RNA", *Helvetica Chimica Acta* 82(12):2151–2159, 1999.

Nielsen et al., "Peptide Nucleic Acids—Protocols and Applications", *Horizon Scientific Press*, pps. 2–3, 1999.

Uhlmann et al., "Antisense Oligonucleotides: A New Therapeutic Principle", *Chemical Reviews* 90(4):543–584, Jun. 1990.

Larsen et al., "Antisense Properties of Peptide Nucleic Acid", *Biochim. Biophys. Acta* 1489(1):159–166, Dec. 10, 1999.

Praseuth et al., "Triple Helix Formation and the Antigene Strategy for Sequence–Specific Control of Gene Expression", *Biochem. Biophys. Acta* 1489(1):181–206, Dec. 10, 1999.

Mischiati et al., "Interaction of the Human NF–$\kappa\beta$ p52 Transcription Factor with DNA–PNA Hybrids Mimicking the NF–$\kappa\beta$ Binding Sites of the Human Immunodeficiency Virus Type 1 Promoter", *J. Biol. Chem.* 274(46):33114–33122, Nov. 12, 1999.

Cole–Strauss et al., "Correction of the Mutation Responsible for Sickle Cell Anemia by an RNA–DNA Oligonucleotide", *Science* 273:1386–1389, Sep. 6, 1996.

Ørum et al., "Labeling of PNA", *Peptide Nucleic Acids: Protocols and Applications*, pps. 81–86, 1999.

Lohse et al., "Fluorescein–Conjugated Lysine Monomers for Solid Phase Synthesis of Fluorescent Peptides and PNA Oligomers", *Bioconjugate Che.* 8(4):503–509, Jul./Aug. 1997.

Wittnug et al., "Phospholipid Membrane Permeability of Peptide Nucleic Acid", *FEBS Lett.* 365(1):27–29, May 22, 1995.

Koch et al., "PNA–Peptide Chimerae", *Tetrahedron Lett.* 36(38):6933–6939, Sep. 18, 1995.

Egholm et al., "Peptide Nucleic Acids (PNA): Oligonucleotide Analogues with an Achiral Peptide Backbone", *J. Am. Chem. Soc.* 114(5):1895–1897, Feb. 26, 1992.

Nielsen et al., Appendix, "Peptide Nucleic Acids—Protocols and Applications", *Horizon Scientific Press*, pps. 253–255, 1999.

Falkiewicz, B., "Peptide Nucleic Acids and Their Structural Modifications", *Acata Biochim. Polonica* 46(3):509–529, 1999.

Sosnowski et al., "Rapid Determination of Single Base Mismatch Mutations in DNA Hybrids by Direct Electric Field Control", *Proc. Natl. Acad. Sci. USA* 94(4):1119–1123, Feb. 1997.

Hung et al., "Comparison of Fluorescence Energy Transfer Primers with Different Donor–Acceptor Dye Combinations", *Analytical Biochemistry* 255(1):32–38, Jan. 1, 1998.

Tarrason et al., "Intracellular Distribution of Digoxigenin–Labeled Phosphorothioate Oligonucleotides", *Methods in Enzymology* 313:257–268, 1999.

Matthes et al., "Telomerase Protein Rather than its RNA is the Target of Phosphorothioate–Modified Oligonucleotides", *Nucleic Acids Research* 27(4):1152–1158, Feb. 15, 1999.

Hayashi et al., "In Vivo Transfer of Gene and Oligodeoxynucleotides into Skin of Fetal Rats by Incubation in Amniotic Fluid", *Gene Therapy* 3(10):878–885, Oct. 1996.

Just et al., "Flow Cytometric Detection of EBV (EBER snRNA) Using Peptide Nucleic Acid Probes", *Journal of Virological Methods* 73(2)163–174, Aug. 1998.

Strother et al., "Synthesis and Characterization of DNA–Modified Silicon (111) Surfaces", *J. Am. Chem.* 122(6)1205–1209, Feb. 16, 2000.

Pirrung, M., "Spatially Addressable Combinatorial Libraries", *Chem. Rev.* 97(2):473–488, Mar./Apr. 1997.

Wang et al., "Peptide Nucleic Acid Probes for Sequence–Specific DNA Biosensors", *J. Am. Chem. Soc.* 118(33):7667–7670, Aug. 21, 1996.

Will et al., "The Synthesis of Polyamide Nucleic Acids Using a Novel Monomethoxytrityl Protecting–Group Strategy", *Tetrahedron* 51(44):12069–12082, Oct. 30, 1995.

Breipohl et al., "Novel Synthetic Routes to RNA Monomers and PNA–DNA Linker Molecules", *Tetrahedron* 53(43):14671–14686, Oct. 27, 1997.

Sonveaux, E., "The Organic Chemistry Underlying DNA Synthesis", *Bioorganic Chemistry* 14(3):274–325, Sep. 1986.

Beaucage et al., "The Functionalization of Oligonucleotides Via Phosphoramidite Derivatives", *Tetrahedron* 49(10):1925–1963, Mar. 5, 1993.

Ravin, L., "Preformulation", *Remington's Pharmaceutical Sciences*, Mack Publishing Company, Easton, PA, pps. 1409–1423, 1985.

Li et al., "Molecular Beacons: A Novel Approach to Detect Protein–DNA Interactions", *Angew. Chem. Int. Ed.* 39(6):1049–1052, Mar. 17, 2000.

Sokol et al., "Real Time Detection of DNA–RNA Hybridization in Living Cells", *Proc. Natl. Acad. Sci. USA* 95(20):11538–11543, Sep. 29, 1998.

Niemeyer et al., "DNA Microarrays", *Angew. Chem. Int. Ed.* 38(19):2865–2869, 1999.

Weiner et al., "Liposomes as a Drug Delivery System", *Drug Develop. and Ind. Pharm.* 15(10):1523–1554, 1989.

\* cited by examiner

Fluorescein (Amide)

Fluorescein (Thiourea)

Tetrachlorofluorescein

Hexachlorofluorescein

Biotin

Dabcyl

Psoralen

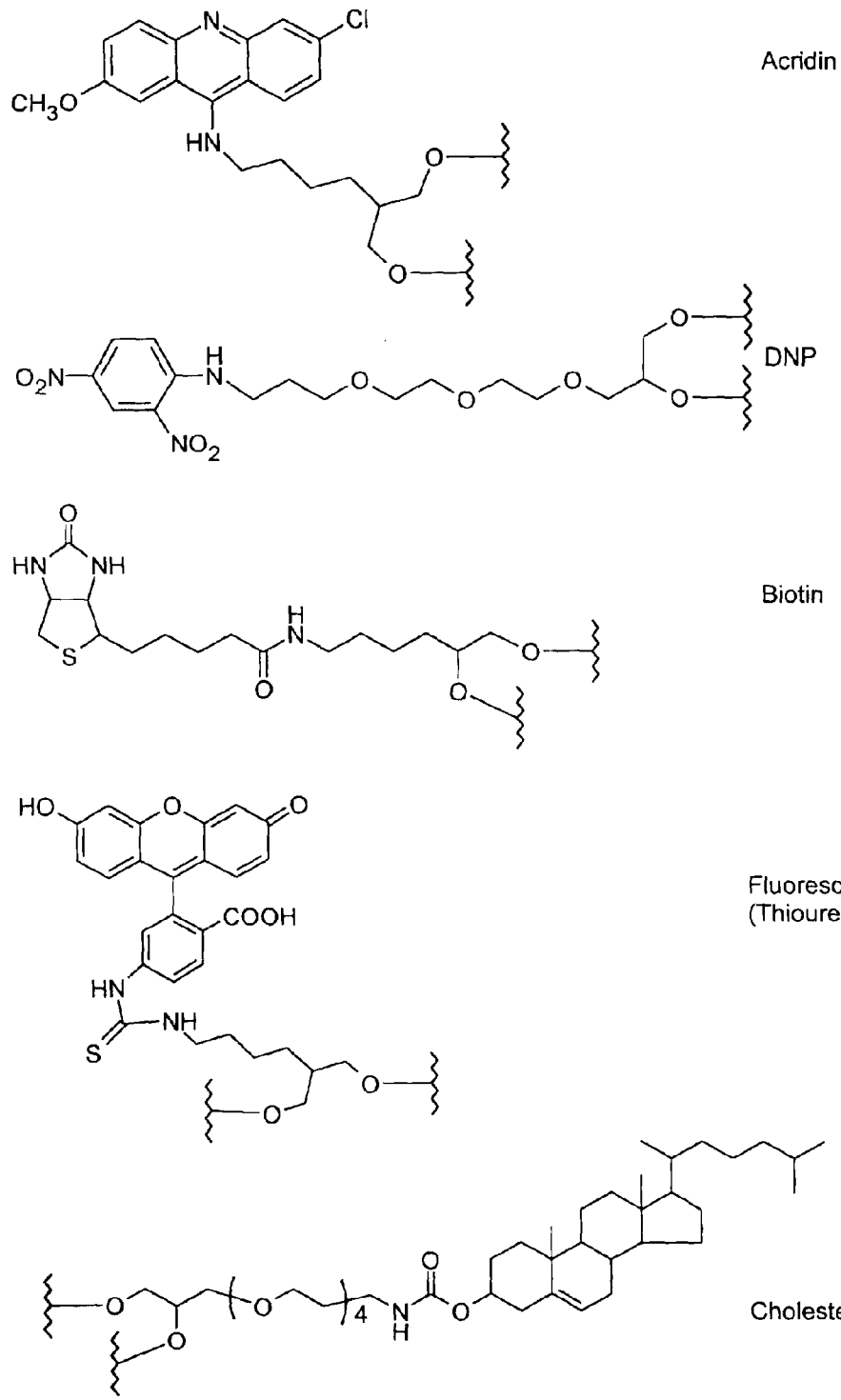

Acridin

DNP

Biotin

Fluorescein (Thiourea)

Cholesterol

Cy3

Cy5

Spacer-9

Spacer-18

TAMRA

Phosphorylating reagent 1

Phosphorylating reagent 2

Fluorescein phosphoramidit 3 (monofunctional)

Fluorescein phosphoramidit 4 (bifunctional)

Biotin phosphoramidit 5 (monofunctional)

Biotin phosphoramidit 6 (bifunctional)

C16-phosphorylating reagent 7

Spacer-9 phosphoramidit 8

Spacer-18 phosphoramidit 9

Cyanin-3 phosphoramidit 10

Cyanin-5 phosphoramidit 11

Aminomodifier-5
phosphoramidit 12

Aminomodifier-C6
phosphoramidit 13

SEQUENCE LISTING

<160> NUMBER OF SEQ ID NOS: 53

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: base
      sequence of PNA targeting viral or cellular targets

<400> SEQUENCE: 1
gcgtttgctc ttcttcttgc g                                              21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 2
acacccaatt ctgaaaatgg                                                20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 3
aggtccctgt tcgggcgcca                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 4
gcggggctcc atggggtcg                                                 20

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 5
cagctgcaac ccagc                                                     15

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence: base
      sequence of PNA targeting CMV

```
<400> SEQUENCE: 6
tattccgtca t                                                          11

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 7
ttccgtcatc gctcctcagg gg                                              22

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 8
ggctgccatg gtccc                                                      15

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 9
ggctgctgga gcggggcaca c                                               21

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 10
aacgttgagg ggcat                                                      15

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 11
gtgccggggt cttcgggc                                                   18

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: base
      sequence of PNA targeting CMV
```

```
<400> SEQUENCE: 12
cgagaacatc atcgtgg                                              17

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:  base
      sequence of PNA targeting CMV

<400> SEQUENCE: 13
ggagaacatc atggtcgaaa g                                         21

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:  base
      sequence of PNA targeting CMV

<400> SEQUENCE: 14
cccgagaaca tcatggtcga ag                                        22

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:  base
      sequence of PNA targeting CMV

<400> SEQUENCE: 15
ggggaaagcc cggcaagggg                                           20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:  base
      sequence of PNA targeting CMV

<400> SEQUENCE: 16
cacccgcctt ggcctcccac                                           20

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence:  base
      sequence of PNA targeting CMV

<400> SEQUENCE: 17
gggactccgg cgcagcgc                                             18

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:  base
      sequence of PNA targeting CMV
```

```
<400> SEQUENCE: 18
ggcaaacttt cttttcctcc                                              20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence:  base
      sequence of PNA targeting CMV

<400> SEQUENCE: 19
gggaaggagg aggatgagg                                               19

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:  base
      sequence of PNA targeting CMV

<400> SEQUENCE: 20
ggcagtcatc cagcttcgga g                                            21

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence:  base
      sequence of PNA targeting CMV

<400> SEQUENCE: 21
tctcccagcg tgcgccat                                                18

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence:  base
      sequence of PNA targeting CMV

<400> SEQUENCE: 22
gcgctgatag acatccatg                                               19

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence:  base
      sequence of PNA targeting CMV

<400> SEQUENCE: 23
ggaggcccga cc                                                      12

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence:  base
      sequence of PNA targeting CMV
```

-continued

```
<400> SEQUENCE: 24
ggtttcggag gc                                                        12

<210> SEQ ID NO 25
<211> LENGTH: 12
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 25
tggtggaggt ag                                                        12

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 26
gcatggtgga gg                                                        12

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 27
ttggcatggt gg                                                        12

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 28
gcctgggacc ac                                                        12

<210> SEQ ID NO 29
<211> LENGTH: 12
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 29
cagcctggga cc                                                        12

<210> SEQ ID NO 30
<211> LENGTH: 12
<212> TYPE: DNA
<213> ORGANISM: Artificial Sequence
<220> FEATURE:
<223> OTHER INFORMATION: Description of Artificial Sequence: base
      sequence of PNA targeting CMV
```

```
<400> SEQUENCE: 30
tgcagcctgg ga                                                              12

<210> SEQ ID NO 31
<211> LENGTH: 12
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 31
gtgcagcctg gg                                                              12

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 32
ggtgcagcct gg                                                              12

<210> SEQ ID NO 33
<211> LENGTH: 12
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 33
atgggtgcag cc                                                              12

<210> SEQ ID NO 34
<211> LENGTH: 12
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 34
ggcttgaaga tg                                                              12

<210> SEQ ID NO 35
<211> LENGTH: 12
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 35
gcagcccccg ca                                                              12

<210> SEQ ID NO 36
<211> LENGTH: 12
<212> TYPE: DNA
<213> ORGANISM: Artificial Sequence
<220> FEATURE:
<223> OTHER INFORMATION: Description of Artificial Sequence: base
      sequence of PNA targeting CMV
```

```
<400> SEQUENCE: 36
gcagcagccc cc                                                    12

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 37
tcccgcctgt gacatgcatt                                            20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 38
gttctcgctg gtgagtttca                                            20

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 39
gcgtgcctcc tcactggc                                              18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 40
gcagtaagca tccatatc                                              18

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 41
gcccaagctg gcatccgtca                                            20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: base
      sequence of PNA targeting CMV
```

```
<400> SEQUENCE: 42
cccccaccac ttcccctctc                                                 20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence:  base
      sequence of PNA targeting CMV

<400> SEQUENCE: 43
ctcccccacc acttcccctc                                                 20

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence:  base
      sequence of PNA targeting CMV

<400> SEQUENCE: 44
gctgggagcc atagcgagg                                                  19

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence:  base
      sequence of PNA targeting CMV

<400> SEQUENCE: 45
actgctgcct cttgtctcag g                                               21

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence:  base
      sequence of PNA targeting CMV

<400> SEQUENCE: 46
caatcaatga cttcaagagt tc                                              22

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence:  base
      sequence of PNA targeting CMV

<400> SEQUENCE: 47
gcggcggaaa agccatcg                                                   18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence:  base
      sequence of PNA targeting CMV
```

```
-continued

<400> SEQUENCE: 48
gtgtcggggt ctccgggc                                               18

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 49
cacgttgagg ggcat                                                  15

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 50
gtcttccata gttactca                                               18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 51
gatcaggcgt gcctcaaa                                               18

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 52
gatggagggc ggcatggcgg g                                           21

<210> SEQ ID NO 53
<211> LENGTH: 11
<212> TYPE: DNA
<213> ORGANISM: Artificial Sequence
<220> FEATURE:
<223> OTHER INFORMATION: Description of Artificial Sequence: base
      sequence of PNA targeting CMV

<400> SEQUENCE: 53
tattccgtca t                                                      11
```

POLYAMIDE NUCLEIC ACID DERIVATIVES, AND AGENTS AND PROCESSES FOR PREPARING THEM

BACKGROUND OF THE INVENTION

1. Field of the Invention

The present invention relates to carboxy-terminally and carboxy/amino-terminally phosphorylated polyamide nucleic acid (PNA) derivatives having improved properties, to their use and to agents and processes for preparing them.

2. Summary of the Related Art

Polyamide nucleic acids, also termed peptide nucleic acids (PNA), bind to complementary target sequences (DNA or RNA) with a higher affinity than do natural oligonucleotides and, furthermore, have the advantage, as compared with natural DNA, that they are very stable in serum. PNA were originally described as unnatural nucleic acid analogs in which the entire sugar-phosphate backbone is replaced with N-(2-aminoethyl)glycine units (M. Egholm et al. (1991) Science 254, 1497–1500; WO 92/20702; M. Egholm et al. Nature (1993) 365, 566–568; P. Nielsen, (1994) Bioconjugate Chem. 5, 3–7; E. Uhlmann et al. (1998) Angewandte Chemie Int. Ed. Engl. 37, 2796–2823). The bases employed are 1) nucleobases which occur naturally and are customary in nucleotide chemistry, 2) nucleobases which do not occur naturally, and 3) the prodrug forms of these two types of bases, that is, precursors which are only converted into the free base by biotransformation in the body.

PNAs have also been described in which not all the positions in the backbone carry base residues (Greiner et al. (1999) Helv. Chim Acta 82, 2151), and in which aminoethylglycine is replaced by more complex units (Uhlmann et al. (1998) Angewandte Chem. Int. Ed. 37, 2796; Falkiewicz (1999) Biochim. Pol., 46, 509–529).

The fact that the PNA backbone does not have any net charge is a feature of this class of substances that has far-reaching consequences. The fact that PNA binds to complementary DNA and RNA even at low salt concentration (see e.g. Peptide Nucleic Acids: Protocols and Applications; Peter E. Nielsen and Michael Egholm (Edit.) Horizon Scientific Press, 1999, page 3), with the Watson-Crick base pairing rules being obeyed, is ascribed to the neutral character of the PNA and the decrease in charge repulsion which is associated therewith. For this reason, PNA can, in principle, be used for numerous applications in which natural oligonucleotides or oligonucleotide derivatives would otherwise be employed. However, in addition to this, because of the unique binding properties, a large number of applications which are not possible with natural oligonucleotides also ensue (see, for example: Peptide Nucleic Acids: Protocols and Applications; Peter E. Nielsen and Michael Egholm (Edit.) Horizon Scientific Press, 1999). For example, a strand invasion of double-stranded DNA has been observed when using PNA, resulting in formation of triplex structures.

Typical examples of applications for PNA include its use for inhibiting gene expression by binding, in a sequence-specific manner, to cellular DNA or RNA. "Antisense agents" are short, single-stranded nucleic acid derivatives which bind, by means of Watson-Crick base pairing, to a complementary mRNA whose translation into the corresponding protein is to be inhibited (Uhlmann and Peyman (1990) Chem. Rev. 90, 543; Larsen et al. (1999) Biochem. Biophys. Acta 1489,159). "Anti-gene agents" bind, byway of Hoogsteen base pairing, in the major groove of the DNA double helix with the formation of a triple helix, resulting in transcription of the genes being inhibited in a sequence-specific manner (Praseuth et al. (1999) Biochem. Biophys. Acta 1489, 181). Gene expression can also be specifically inhibited by so-called decoy oligomers, which mimic the regions for binding transcription factors. By treating with decoy agents, particular transcription factors can be captured in a sequence-specific manner and activation of transcription thereby prevented (Mischiati et al. (1999) J. Biol. Chem. 274, 33114). Another group of oligonucleotide derivatives which act intracellularly are the chimeraplasts. These are used for specific gene proof-reading (Cole-Strauss et al. (1996) Science 273, 1386–1389).

PNAs can, therefore, be used as pharmaceuticals and/or diagnostic agents or for producing pharmaceuticals and/or diagnostic agents. For example, after having been labeled with biotin, fluorescein, or other labels, PNA can be used as a specific hybridization probe for diagnostic purposes and in molecular biology.

Four methods have so far been described in the literature for introducing the labeling groups (Oerum et al. (1999), in Peptide Nucleic Acids: Protocols and Applications, pages 81–86; Lohse et al. (1997) Bioconjugate Chem. 8, 503). The first method is based on labeling the free (deprotected) PNA after it has been synthesized in solution. In this method, the amino terminus of the PNA is reacted with an activated carboxylic acid or an isothiocyanate. However, additional lysine residues are frequently introduced into the PNA, with these residues then being reacted with fluorescein isothiocyanate (FITC).

In the second method, the protected PNA is modified at its amino terminus with activated carboxylic acid derivatives or isothiocyanates while it is still on the solid phase. This method is only suitable for labeling groups which are stable under the conditions which pertain during deprotection of the PNA and during its cleavage from the support. The reactive reagents which are preferably used in both cases are isothiocyanates (P. Wittung et al., (1995) FEBS Lett. 375, 27) and activated carboxylic acids, such as N-hydroxysuccinimide esters (NHS) (Oerum et al., 1999). A disadvantage of the reaction using the NHS derivatives is that it is frequently only accomplished with poor yields. For this reason, 8-amino-3,6-dioxaoctanoic acid is frequently condensed, as a linker or spacer, between the PNA and the labeling group (Oerum et al., 1999). Both linkages are effected by way of amide bonds or thiourea bonds, which, as such, are, however, more likely to lead to insolubility. Alternatively, the carboxylic acids are caused to react using activators which are customary in peptide chemistry, such as HBTU, TBTU or HATU.

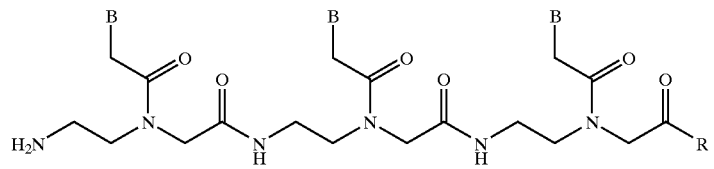

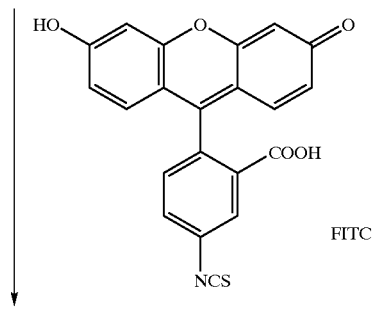

FITC

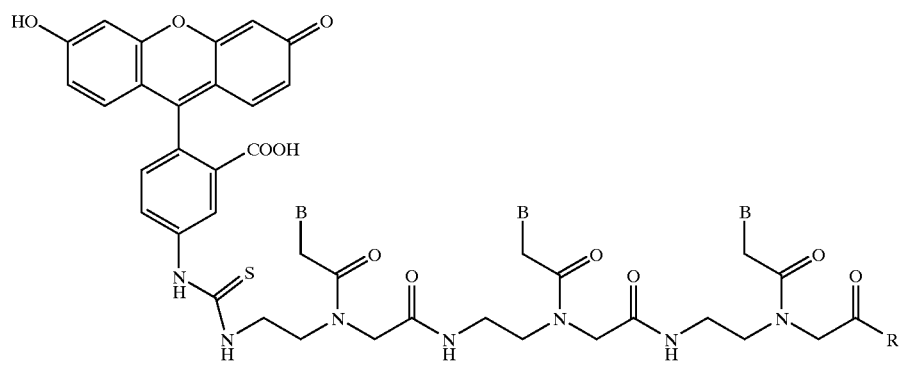

In a third method, shown generally above, fluorescein-conjugated monomers are used during the synthesis of the PNA on the solid phase, with the fluorescence labeling being effected by way of an amide bond (Lohse et al. (1997) Bioconjugate Chem. 8, 503), which once again leads to conjugates that are relatively difficult to dissolve.

A fourth method uses PNA peptide conjugates in which the peptide moiety forms a substrate for a protein kinase (Koch et al. (1995) Tetrahedron Lett. 36, 6933). In this way, therefore, it is not the PNA moiety which is modified; rather, the serine residue in the peptide segment is phosphorylated enzymatically. When this method is used, therefore, it is only possible to introduce radioactive phosphate, and not, for example, any fluorescein or biotin, into the peptide segment of the PNA-peptide conjugate. The general reaction is depicted as follows:

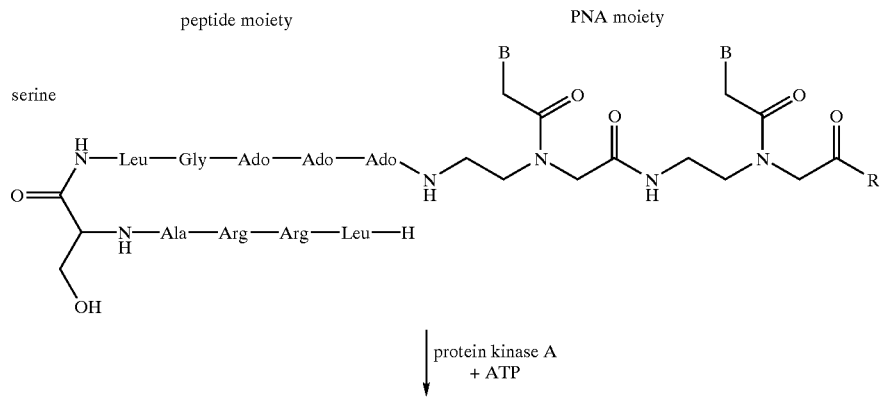

-continued

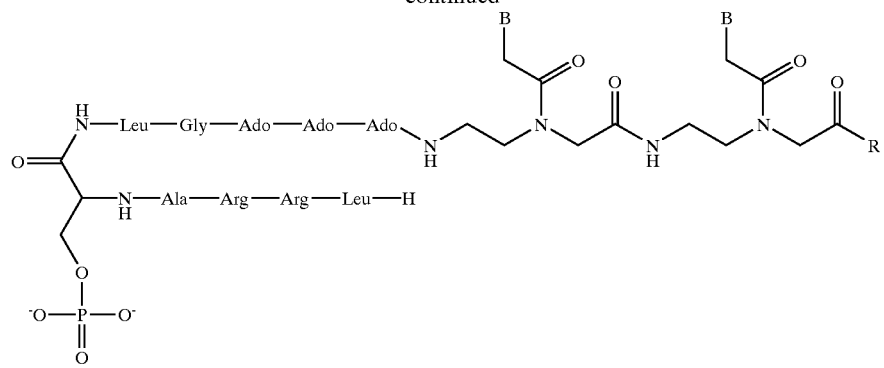

It is known that PNA tends to aggregate in aqueous solution, that is, under physiological conditions as well. PNA is therefore poorly soluble in aqueous buffer and is then unavailable for hybridizing to complementary sequences. Furthermore, PNA has a high affinity for various materials such as SEPHADEX® (from Pharmacia), BOND ELUT® (from Varian), or various HPLC chromatograph materials that are used in purifying oligomers. This means that PNA can frequently only be isolated in poor yields. It is therefore necessary to conjugate PNA with lysine or other positively charged amino acids (by way of the C terminus) (Egholm et al (1992) J. Am. Chem. Soc. 114, 1895). Guanine-rich PNA sequences have a very particular tendency to aggregate. For this reason, use of such PNA is generally discouraged (see "Guidelines for sequence design of PNA oligomers" in Peptide Nucleic Acids: Protocols and Applications (1999) pages 253–255). For example, relatively long fluorescein-labeled PNA oligomers are particularly difficult to dissolve, with the addition of an organic solvent and heating to 50° C. being recommended.

It is particularly difficult to purify the poorly soluble lipophilic PNA derivatives. Several peaks due to PNA aggregates are frequently detected in the HPLC. The technique of polyacrylamide (PAA) gel electrophoresis, which is frequently employed for purifying and separating nucleic acids, cannot be used for these PNA derivatives.

In the methods of derivatizing PNA which are described above, the labeling group is always introduced by forming an amide bond or a thioamide bond, with PNA derivatives being formed which are relatively difficult to dissolve. Poorly soluble PNA derivatives are formed, in particular, when lipophilic residues, such as fluorescein, are introduced. Inserting labels at both ends of the PNA is technically even more difficult and generally leads to even poorer solubility. In addition, no efficient method for simultaneously derivatizing PNA at the amino and carboxy termini, in particular by means of solid phase synthesis, has been described. Furthermore, since the labeling reactions frequently proceed with poor yields, there is a need in the art to develop PNA derivatives that can be prepared in high yields, and which should exhibit advantageous properties, such as improved solubility, improved binding behavior, and better cellular uptake, and which, in addition, make it possible to use efficient methods for purifying the PNA oligomers.

BRIEF DESCRIPTION OF THE DRAWINGS

FIGS. 2a and 3a show examples of bridging X and X' radicals.

DETAILED DESCRIPTION OF THE INVENTION

Figure 1A:
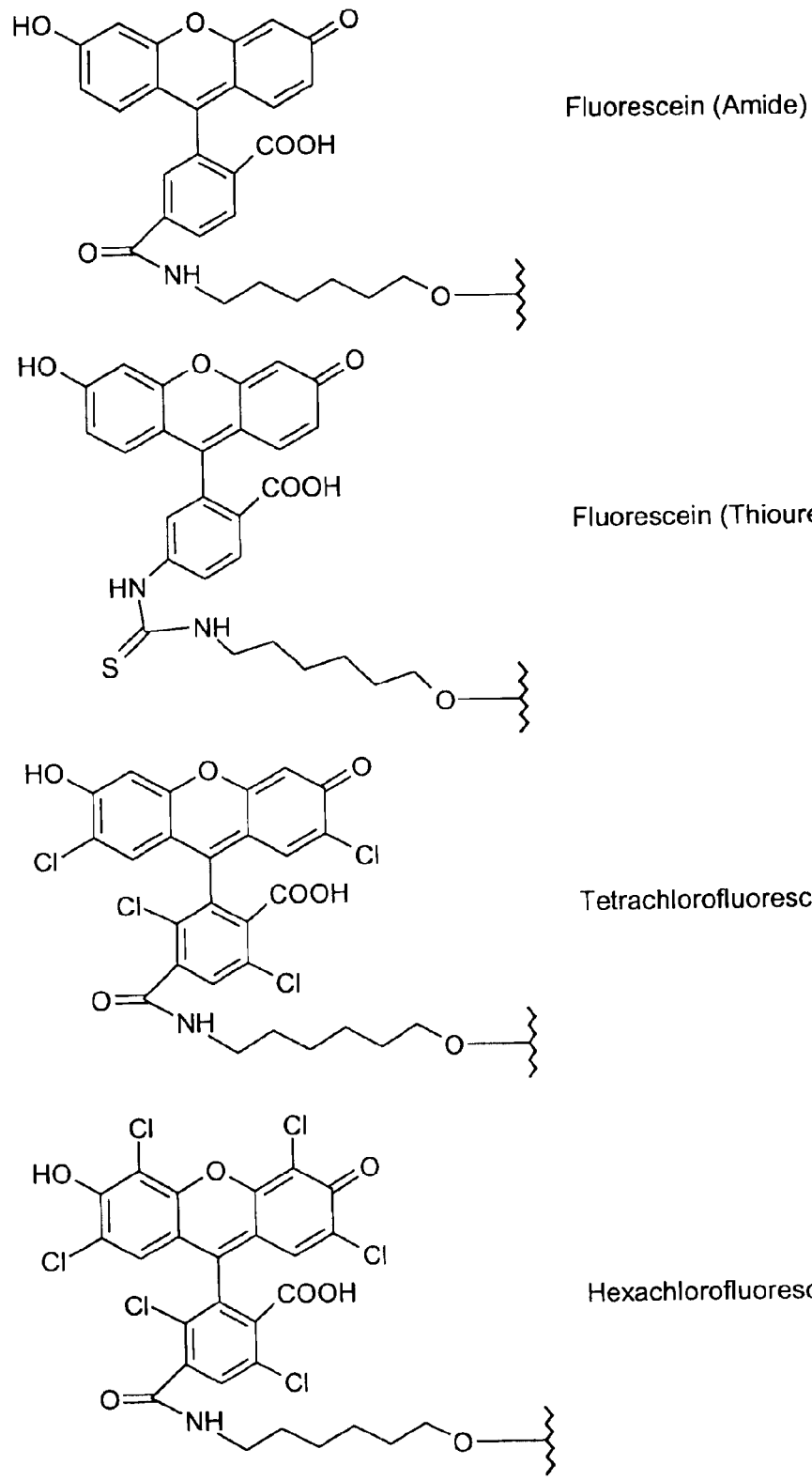
FIGS. 1a, 1b, 2b and 3b show examples of terminal Z and Z' radicals.
Figure 1B:
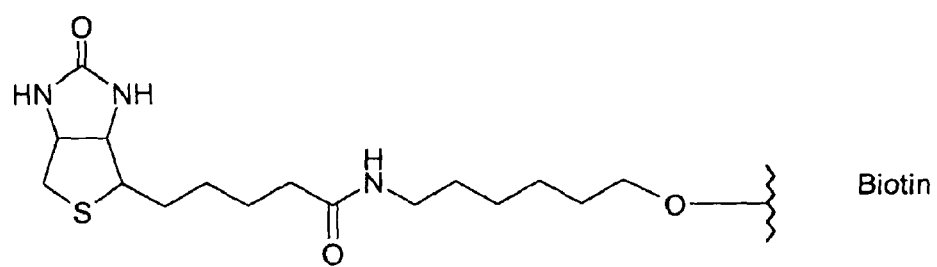
Figure 1B:
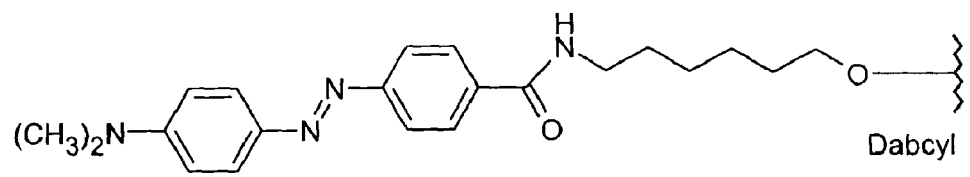
Figure 1B:
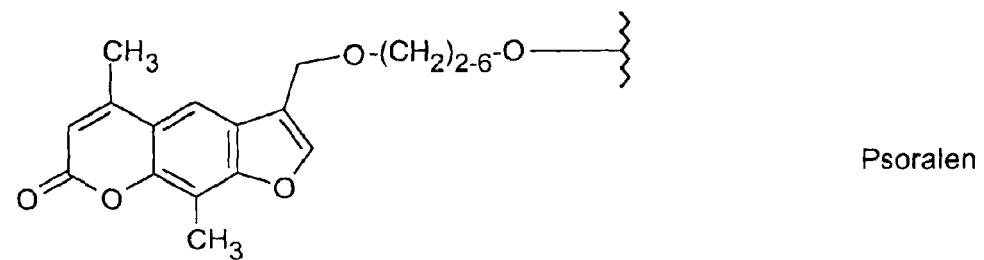
Figure 2B:
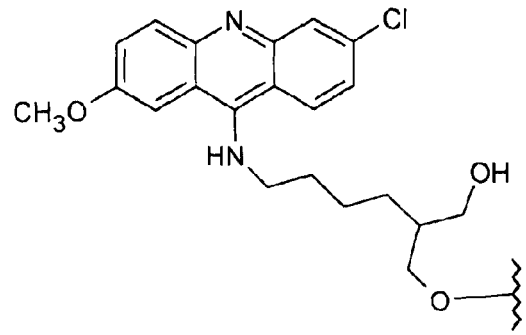
Figure 2B:
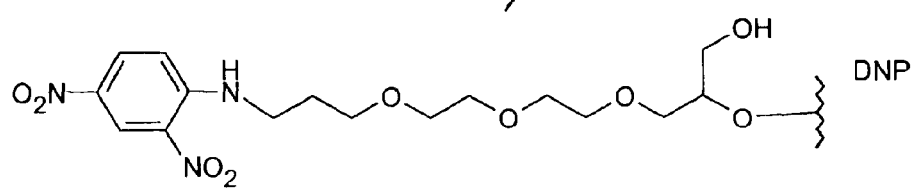
Figure 2B:
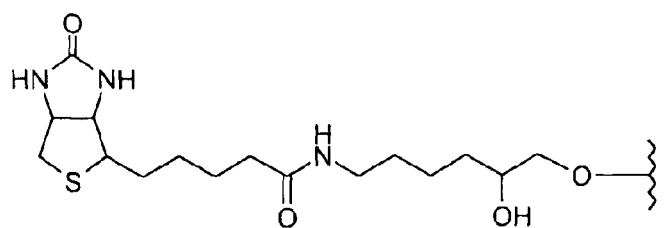
Figure 2B:
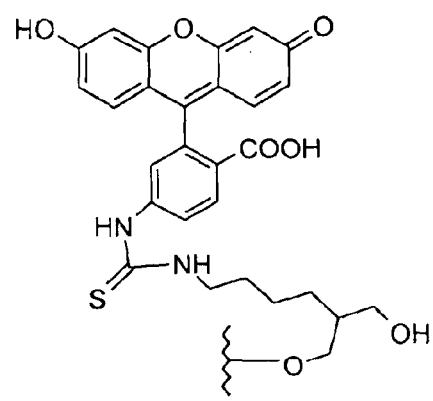
Figure 2B:
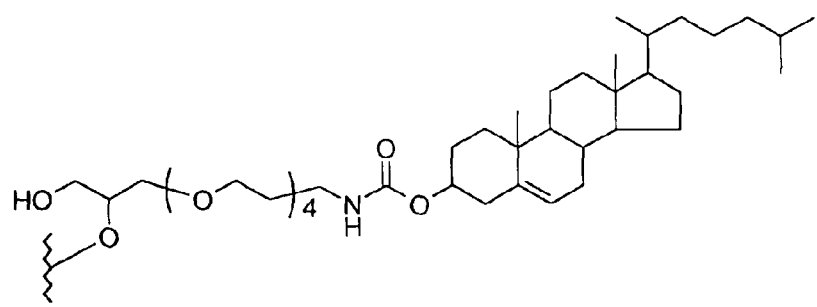
Figure 3A:
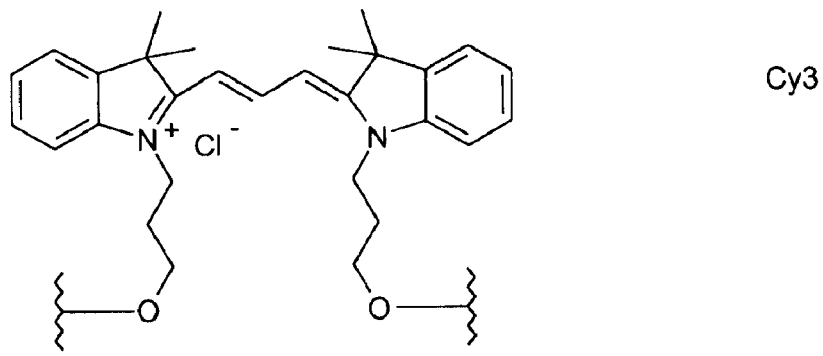
Figure 3A:
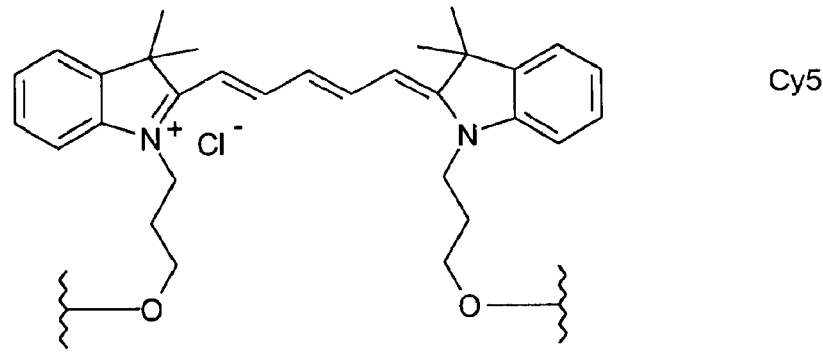
Figure 3A:
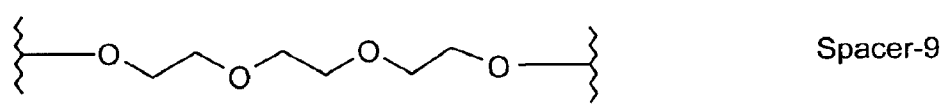
Figure 3A:
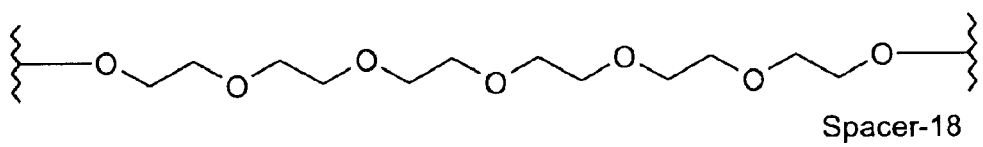
Figure 3A:
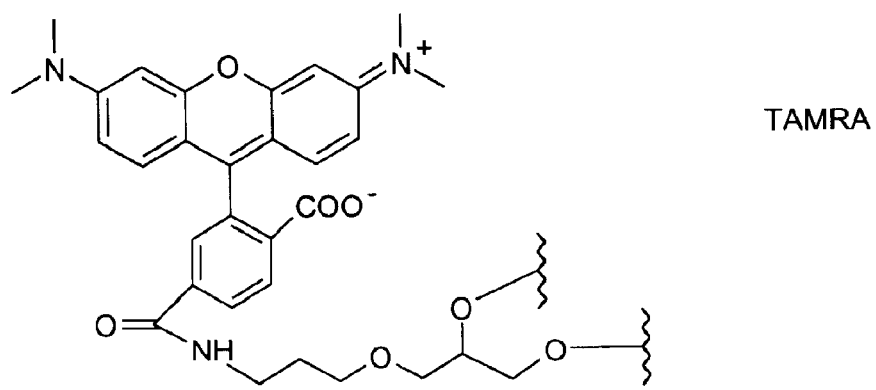
Figure 3B:
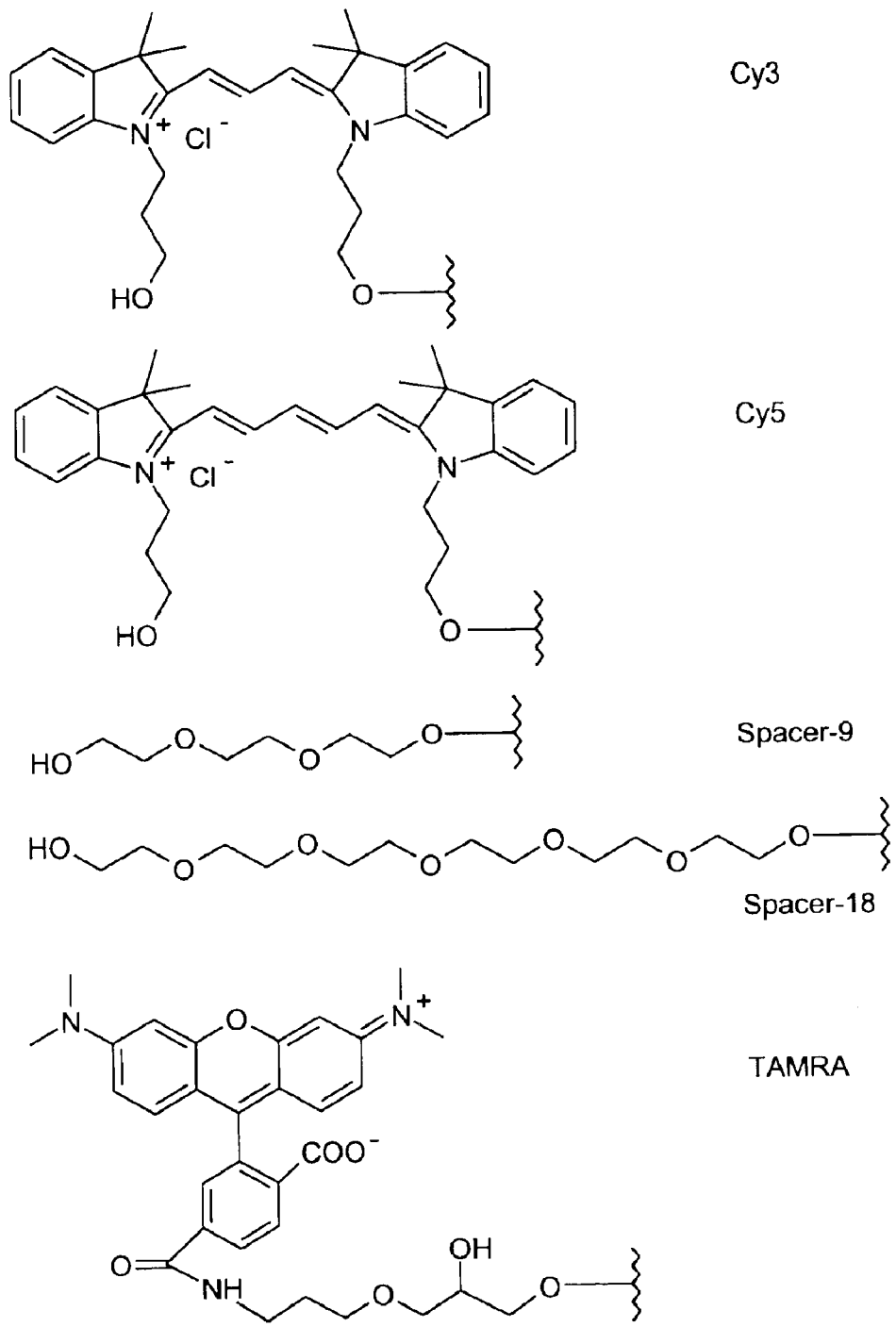
Figure 4A:
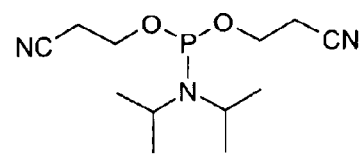
FIGS. 4a, 4b, 4c and 4d show examples of phosphorylating reagents.
Figure 4A:
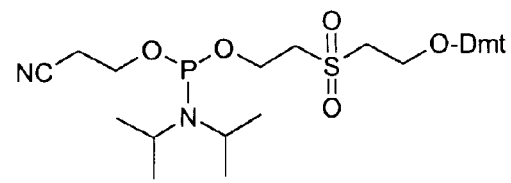
Figure 4A:
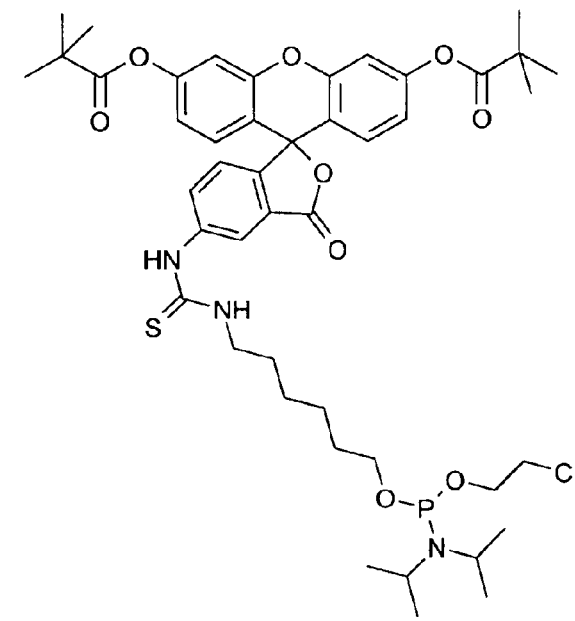
Figure 4B:
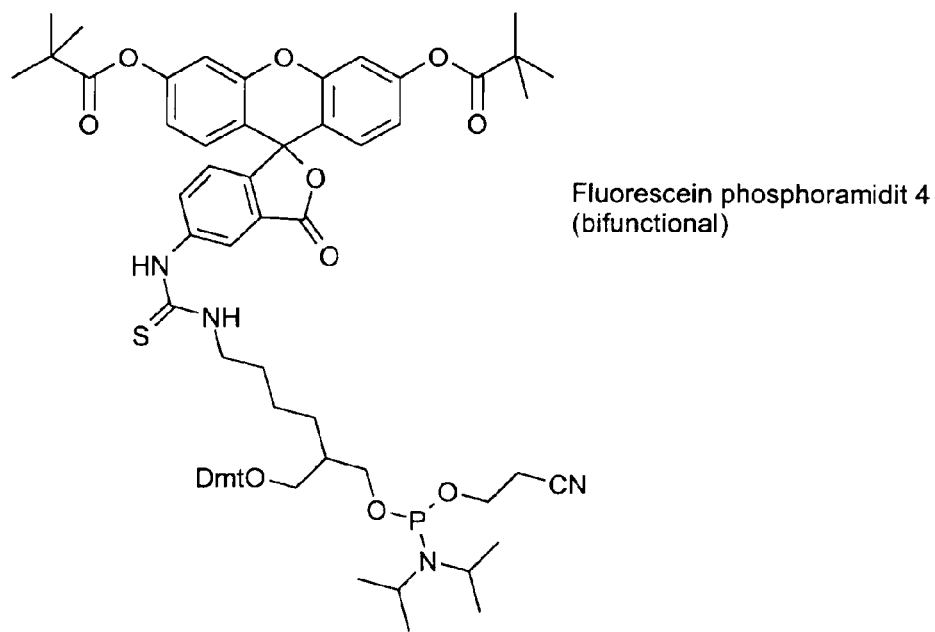
Figure 4B:
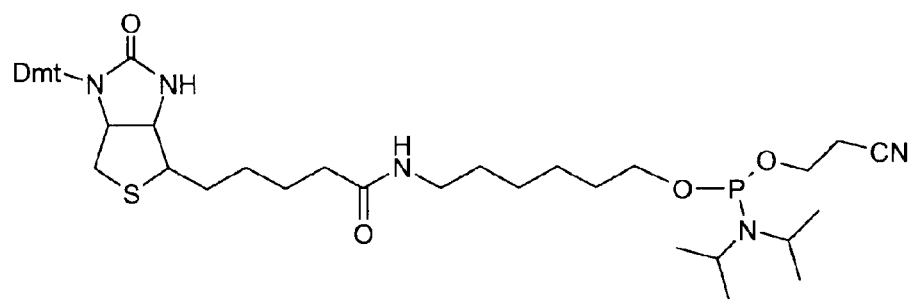
Figure 4B:
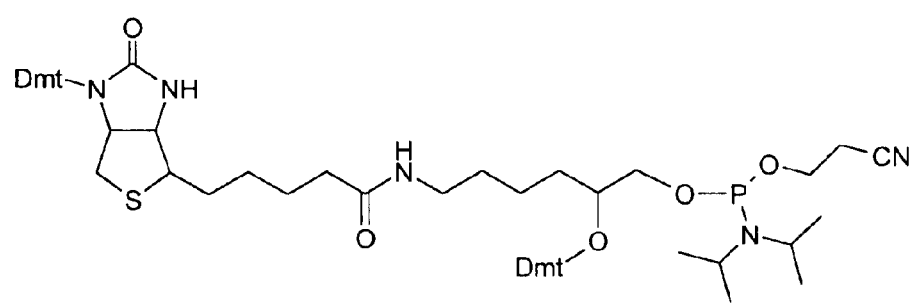
Figure 4C:
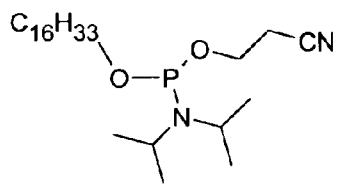
Figure 4C:
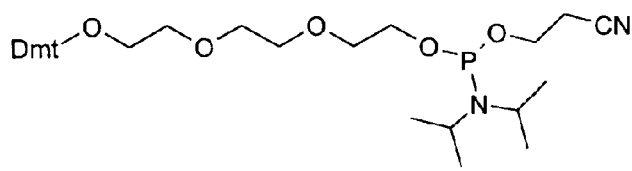
Figure 4C:
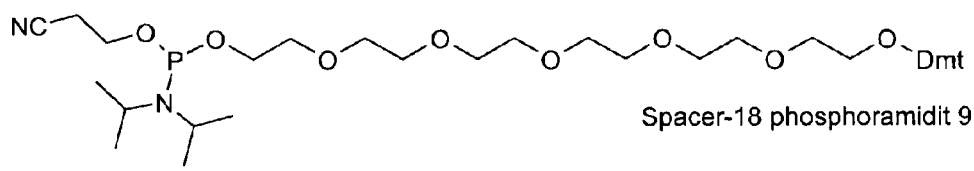
Figure 4C:
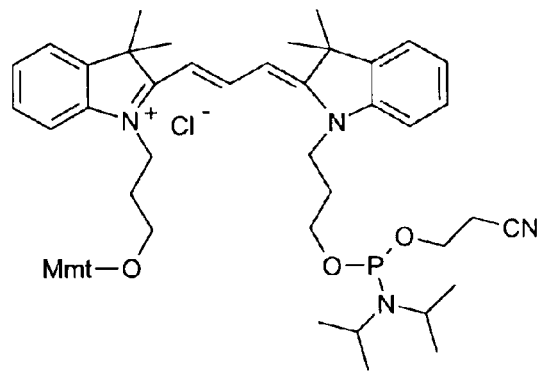
Figure 4C:
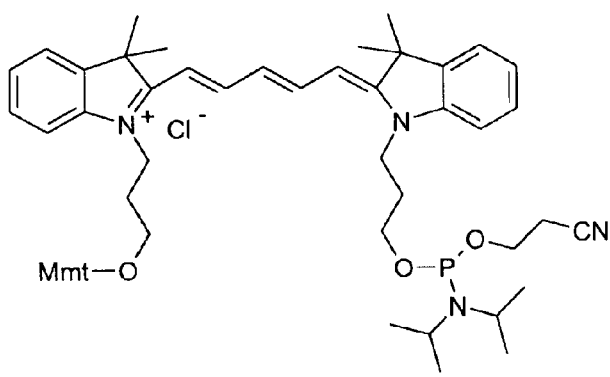
Figure 4D:
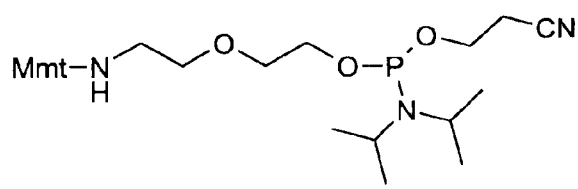
Figure 4D:
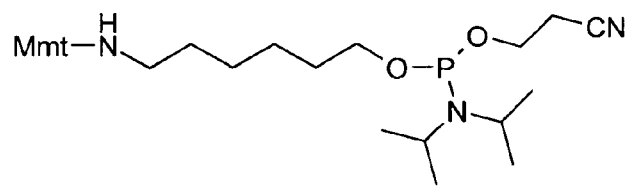

According to the invention, the needs of the art are achieved by providing PNA derivatives which carry one or more phosphoryl radicals at the C terminus or at the C and N termini of the PNA backbone. The invention provides PNA derivatives that are derivitized with, among other things, thiophosphoryl radicals, iminophosphoryl radicals, and/or oxophosphoryl radicals. The PNA derivatives of the invention can have at least one of the phosphoryl radicals carrying one or more deprotonatable groups, such as hydroxyl groups or mercapto groups. The phosphoryl radicals can be linked to the PNA backbone by way of an oxygen-phosphorus bond, sulfur-phosphorus bond, or nitrogen-phosphorus bond, either directly or by way of a spacer. The spacer can be, but is not necessarily, an alkanoylamide, a poly(alkoxy)carboxamide, or an amino acid. Examples of phosphoryl radicals include, but are not limited to, phosphate, phosphonate, thiophosphate, phosphoamidate, and substituted phosphoryl radicals. The substituted phosphoryl radicals can carry, where appropriate, one or more labeling groups, groups for crosslinking, groups which promote intracellular uptake, or groups which increase the binding affinity of the PNA derivative for nucleic acids.

Thus, in embodiments, the invention is directed to a PNA derivative which carries one or more phosphoryl radicals at the C terminus or at the C and N termini of the PNA backbone, wherein the phosphoryl radicals comprise oxo-, thio- and imino-phosphoryl radicals, and wherein at least one of the phosphoryl radicals carries one or more deprotonatable groups, and wherein the phosphoryl radicals are linked to the PNA backbone by way of an oxygen-phosphorus bond, a sulfur-phosphorus bond, or a nitrogen-phosphorus bond, either directly or by way of a spacer.

Labeling groups (labels) are understood as being groups which enable the chemical or biological activity of the PNA derivatives to be assessed qualitatively or quantitatively, for example biotin or fluorescein. Crosslinking is understood as being the formation of intramolecular or intermolecular bonds between spatially adjacent functionalities. An example of a group for crosslinking is the psoralen group.

In general, the invention relates to PNA derivatives of Formula I

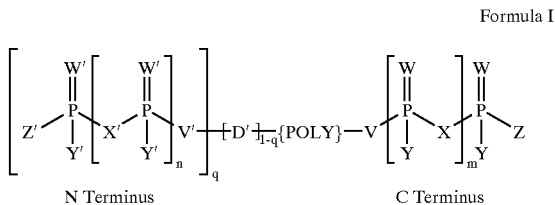

Formula I

N Terminus                     C Terminus wherein q is 0 or 1,

D' is hydroxyl, mercapto, amino, alkylamino, or acylamino, such as acetylamino,

V is oxygen, sulfur, or $NR_1$,

V' is, independently of any other V', oxygen, sulfur, $NR_1$, $U—(CR_3R_4)_{u'}—C(O)—NH$, or $U—(CH_2CH_2O)_{u'}—CH_2—C(O)—NH$, U is, independently of any other U, oxygen, sulfur, or NH, u' is, independently of any other u', from 1 to 10, such as from 1 to 4, for example, 1, W and W' are, independently of each other, oxygen, sulfur, or $NR_1$, Y and Y' are, independently of each other, hydroxyl, mercapto, oxyanion, thioate, or $NR_1R_2$, X and X' are, independently of each other, $U—(C_2-C_{22}$-alkanediyl)-U, $U—(CH_2CH_2—O)_{u'}$, a labeling group, a group for crosslinking, a group which promotes intracellular uptake, or a group which increases the binding affinity of the PNA derivative for nucleic acids, for example a bifunctional fluorescein, rhodamine, TAMRA, biotin, pyrene, dinitrophenyl, cholesteryl, acridine, adamantyl, vitamin E, cyanine dye, dabcyl, edans, lexitropsin, psoralen, BODIPY, ROX, R6G or digoxygenin radical, Z and Z' are, independently of each other, hydroxyl, mercapto, oxyanion, thioate, $NR_1R_2$, $C_1-C_{22}$-alkyl, $C_1-C_8$-arylalkyl, $C_1-C_{22}$-alkyl-U, $C_1-C_8$-arylalkyl-U, hydroxy-$C_1-C_{18}$-U, aminoalkyl-U, mercaptoalkyl-U, a group of the formula $R_7(CH_2CH_2—O)_{m'}$, wherein $R_7$ is hydroxyl, amino, or $C_1-C_{22}$-alkoxy, and m' is from 1 to 100, such as from 2 to 10, a labeling group, a crosslinking group, a group which promotes intracellular uptake, or a group which increases the binding affinity of the PNA derivative for nucleic acids, for example a monofunctional or bifunctional fluorescein, rhodamine, TAMRA, biotin or a biotin derivative, pyrene, dinitrophenyl, cholesteryl, acridine, adamantyl, vitamin E, cyanine dye, dabcyl, edans, lexitropsin, psoralen, BODIPY, ROX, R6G or digoxygenin radical, $R_1$ and $R_2$ are, independently of each other, a radical consisting of hydrogen or $C_1-C_6$-alkyl, for example hydrogen, $R_3$ and $R_4$ are, independently of each other, a radical consisting of hydrogen, or $C_1-C_6$-alkyl, or the radical of an amino acid side chain, for example hydrogen, it being possible for adjacent radicals $R_3$ and $R_4$ in V' to also form a $C_5-C_8$-cycloalkyl ring, n is from 0 to 10, such as from 0 to 3, m is from 0 to 10, such as from 0 to 3, with the proviso that at least one of the Y, Y', Z, or Z' radical is hydroxyl, mercapto, oxyanion, or thioate;

and wherein {POLY} is described by Formula II,

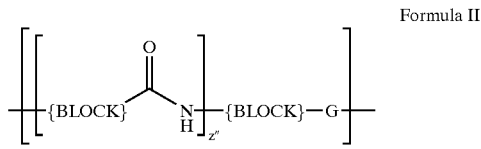

Formula II wherein {BLOCK} is, independently of any other {BLOCK}, Formula IIIA,

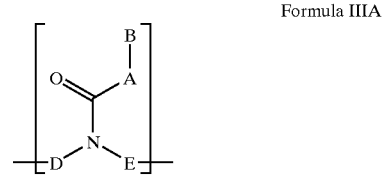

Formula IIIA

Formula IIIB (Greiner et al. (1999) Helv. Chim Acta 82, 2151),

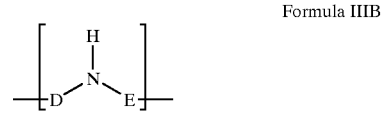

Formula IIIB or Formulae IV A to IV G (Uhlmann et al. (1998) Angewandte Chem. Int. Ed. 37, 2796; Falkiewicz (1999) Biochim. Pol., 46, 509–529),

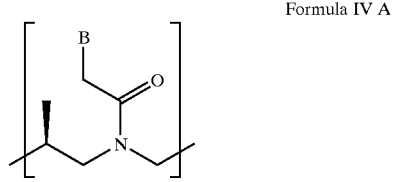

Formula IV A

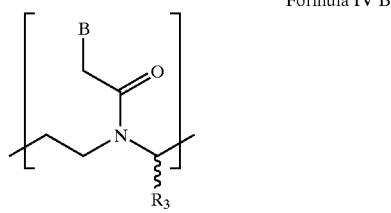

Formula IV B

-continued

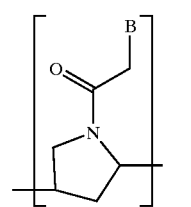

Formula IV C

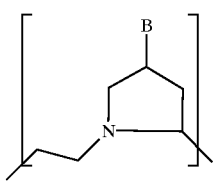

Formula IV D

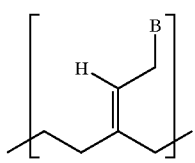

Formula IV E

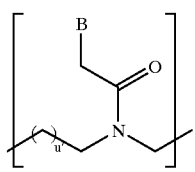

Formula IV F

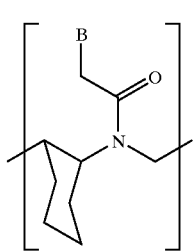

Formula IV G wherein each {BLOCK} building block can be different; and wherein

Z" is from 0 to 100, such as 1–20, for example 4–15,

G is selected from the groups $(CR_5R_6)_{u'}$, $C(O)NH—(CR_1R_2)_{t'}$, or $C(O)NH—(CH_2CH_2O)_{u'}—CH_2CH_2$, wherein u' has the above-mentioned meaning and t' is from 2 to 10, for example 6, A is, independently of any other A, a group $(CR_1 R_2)_s$, wherein s is from 1 to 3, for example 1, B is, independently of any other B, either an aromatic radical which optionally possesses heteroaromatic character, hydrogen, hydroxyl, or $C_1$–$C_{18}$-alkyl, or a nucleobase which occurs naturally, and is customary in nucleotide chemistry, or which does not occur naturally, or its prodrug form, D with the proviso that at least one B radical is a nucleobase, D is, independently of any other D, a group $(CR_3R4)_t$, wherein t is from 2 to 10, such as from 2 to 4, for example 2, E is, independently of any other E, a group $(CR_5R_6)_{u'}$, wherein adjacent $R_5$ and $R_6$ radicals can also form a $C_5$- to $C_8$-cycloalkyl ring or a spiro compound, $R_5$ and $R_6$ are, independently of each other, a radical consisting of hydrogen, $C_1$–$C_6$-alkyl, or the radical of an amino acid side chain, for example hydrogen, wherein u', $R_1$, $R_2$, $R_3$, and $R_4$ are as defined above.

In addition, the invention relates to physiologically tolerated salts of the PNA derivatives of Formula I. Physiologically tolerated salts are described, for example, in Remington's Pharmaceutical Science (1985) Mack Publishing Company, Easton, Pa., USA, page 1418. In embodiments, the salts are ammonium salts, trialkylammonium salts, alkali metal salts (such as sodium salts and potassium salts), and alkaline earth metal salts (such as magnesium salts and calcium salts). In embodiments, the salts are sodium salts.

A surprising, positive effect which was found was that the introduction of a phosphoryl radical, for example as phosphate or else in the form of a lipophilic derivatization (e.g. as a hexadecyl phosphodiester) increases the affinity of the PNA for complementary DNA or RNA. This effect was unexpected since the strong bonding of PNA to complementary DNA or RNA was attributed to the neutral character of the PNA and the reduced charge repulsion which was associated therewith (e.g. Peptide Nucleic Acids: Protocols and Applications; Peter E. Nielsen and Michael Egholm (Edit.) Horizon Scientific Press, 1999, page 3).

The biotin was introduced particularly efficiently by way of a phosphoryl radical. When used as hybridization probes, the biotinylated PNA of Formula I (X, X', Z, and/or Z'=biotin radical) displayed better binding properties and fewer spurious, nonspecific background effects than did corresponding biotinylated DNA probes.

In contrast to the uncharged PNA, the PNA derivatives of Formula I according to the invention can also migrate in an electric field, thereby making it possible to microlocate them and concentrate them on immobilized complementary nucleic acid derivatives. In the case of polyanionic oligonucleotides, the use of an electrical field for microlocation and concentration has already been described for rapidly determining base mismatches (Sosnowski et al. (1997) Proc. Natl. Acad. Sci. U.S.A. 94, 1119).

The hydroxy or mercapto substituents of the phosphoryl radicals of the DNA derivatives according to the invention can be deprotonated in a pH range of from 4.5 to 14. In embodiments, they are deprotonated in a pH range of from 6.5 to 12, such as from 6.5 to 9. The property of the ionizability of the phosphoryl radicals can advantageously be exploited for purifying the compounds of Formula I. On the one hand, the compounds of Formula I can be purified by electrophoresis, for example polyacrylamide gel electrophoresis (PAGE). On the other hand, it is also possible to purify them using anion exchangers. In the latter case, the desired products can be eluted by using a salt gradient, for example a sodium chloride gradient. They can also be eluted by using a pH gradient. The PNA derivatives of Formula I according to the invention can be simply and efficiently purified using anion exchangers. It was found that the uncharged byproducts are not retarded on the anion exchanger, whereas the charged product adhered to the column. After washing with water, it was possible to isolate the desired product in pure form using acetic acid or a sodium chloride solution. The anion exchangers employed can be strong anion exchangers or mixed-mode phases, such as OASIS MAX® (Waters GmbH, Eschborn).

It was furthermore found that the compounds of Formula I according to the invention are, in general, more readily soluble in aqueous medium than are the corresponding PNA oligomers which do not possess the phosphoryl radical. This is particularly apparent in the form of a greatly improved solubility in aqueous medium in the case of the lipophilic derivatives, such as the fluorescein derivatives or the hexadecyl derivatives.

The invention relates, in embodiments, to PNA derivatives in which A and E of Formula IIIA and/or Formula IIIB are $CH_2$. The invention furthermore relates, in embodiments, to PNA derivatives in which D substituents of Formula IIIA and/or Formula IIIB are $(CH_2)_2$. In embodiments, the invention relates to PNA derivatives of Formula I in which W and W' are oxygen. In embodiments, the invention relates to PNA derivatives of Formula I in which Y and Y' are hydroxyl or oxyanion. In embodiments, the invention relates to PNA derivatives of Formula I in which V and V' are oxygen radicals.

Non-exclusive examples of natural bases are adenine, cytosine, 5-methylcytosine, guanine, thymine, and uracil. Non-exclusive examples of unnatural bases are purine, 2,6-diaminopurine, $N^4N^4$-ethanocytosine, $N^6N^6$-ethano-2,6-diaminopurine, 5-($C_3$–$C_6$)-alkynyluracil, 5-($C_3$–$C_6$)-alkynylcytosine, 5-(1-propargylamino)uracil, 5-(1-propargylamino)cytosine, phenoxazine, 9-aminoethoxyphenoxazine, 5-fluorouracil or pseudoisocytosine, 5-(hydroxymethyl)uracil, 5-aminouracil, pseudouracil, dihydrouracil, 5-($C_1$–$C_6$)-alkyluracil, 5-($C_1$–$C_6$)-alkylcytosine, 5-($C_2$–$C_6$)-alkenylcytosine, 5-fluorocytosine, 5-chlorouracil, 5-chlorocytosine, 5-bromouracil, 5-bromocytosine, 7-deazaadenine, 7-deazaguanine, 8-azapurine, and 7-deaza-7-substituted purines.

In the case of PNA derivatives which only carry a phosphoryl radical at the C terminus (and for which q is 0), the N terminus can be linked to a peptide sequence. Suitable peptide sequences are those which optimize the organ distribution or the cellular location of the PNA, such as transportan, insulin-like growth factor, nuclear localization signals, or other carrier sequences (Larsen et al. (1999) Biochim. Biophys. Acta 159–166). The peptide can also be used as an affinity tag, like, for example, a $(His)_6$ chain.

The present invention enables the X, X', Z, and Z' radicals to be varied broadly (non-limiting examples are given in FIGS. 1a, 1b, 2a, 2b, 3a, and 3b) and thereby makes it possible to introduce different specific functional features into the PNA.

One embodiment of Z or Z' is a $C_1$- to $C_{22}$-alkyl radical. In other embodiments, Z or Z' is a $C_1$- to $C_{22}$-alkoxy radical, for example a $C_{16}$-alkoxy radical. Other suitable radicals include, but are not limited to, hydroxy-($C_1$–$C_{18}$-alkoxy) radicals, such as $HO(CH_2)_{3-12}O$. In embodiments, Z or Z' is an aminoalkoxy radical, such as a 6-aminohexoxy or 5-aminopentoxy radical. In embodiments, Z or Z' is a radical of the formula $R_7(CH_2CH_2—O)_m$, wherein $R_7$ is hydroxyl, amino, or $C_1$–$C_{22}$-alkoxy. In embodiments, $R_7$ is hydroxyl. In embodiments, m is from 0 to 100. In embodiments, m is from 2 to 10. In embodiments, Z or Z' is $HO(CH_2CH_2—O)_2$, $HO(CH_2CH_2—O)_6$, or $H_2N—(CH_2CH_2—O)_2$. In other embodiments, Z or Z' is a mercaptoalkoxy radical, such as 6-mercaptohexyloxy.

In another embodiment, Z or Z' comprises a fluorescent group, such as fluorescein, rhodamine, TAMRA, or a cyanine dye. Non-limiting examples of suitable fluorescent groups can be found in FIGS. 1a to 3b. In embodiments, Z is biotin or a biotin derivative. In yet other embodiments, Z is dabcyl, psoralen, acridine, DNP, cholesterol (see, for example, FIGS. 1b and 2b), BODIPY, ROX or R6G radicals (Su-Chun Hung et al. (1998) Analytical Biochemistry 255, 32–38), or digoxygenin (Tarrason et al., Methods in Enzymology (1999) Vol. 313, 257–268).

In addition to this, Z or Z' can be a group consisting of a monofunctional or a bifunctional fluorescein, rhodamine, TAMRA, biotin, pyrene, dinitrophenyl, cholesteryl, acridine, adamantyl, vitamin E, cyanine dye, dabcyl, edans, lexitropsin, or psoralen radical. Monofunctional end groups are listed by way of example in FIGS. 1a, 1b, 2a and 3a, while bifunctional bridging groups are listed by way of example in FIGS. 2b and 3b. In another embodiment, n and/or m, independently of each other, are 0, i.e. the PNA moiety carries in each case only one phosphoryl radical on the N and/or on the C terminus.

In an embodiment, X or X' is U—($C_2$–$C_{22}$-alkanediyl)-U, such as O—($C_2$–$C_{22}$-alkanediyl)-O. For example X or X' can be O—$(CH_2)_{2-6}$—O. In another embodiment, X or X' is a group of the Formula U—$(CH_2CH_2—O)_{u'}$, wherein u' is from 1 to 10, such as from 1 to 6. In embodiments, U can be oxygen. In a further embodiment, X or X' comprises a fluorescent group such as fluorescein, rhodamine, TAMRA, or a cyanine dye, for example Cy3® (from Amersham Pharmacia Biotech). Exemplary bifunctional groups can be found in FIGS. 2a and 3a. In embodiments, X or X' is biotin. Other groups which are suitable are dabcyl, psoralen, acridine, DNP, cholesterol, BODIPY, lexitropsin, digoxygenin, and ROX and R6G radicals.

The different radicals for X, X', Z, and Z' in Formula I can fulfill different functions. The fluorescein radicals have far-reaching applications in DNA sequencing and signal amplification or as markers for determining the cellular uptake of PNA. The cyanine dye radicals (Cy3® and Cy5®) give a substantially more intense and longer-lasting fluorescence signal than does fluorescein itself. The psoralen radical can be employed for crosslinking with complementary nucleic acids. The acridine radical is an effective intercalator and can thereby augment the binding affinity of the PNA. Biotin, acridine, and psoralen derivatives can also be used for antisense experiments. In addition, hexadecyloxy and cholesterol derivatives can be used for increasing the ability of the PNA to traverse membranes. DNP-labeled compounds of Formula I can be detected using anti-DNP antibodies. Aminoalkoxy radicals can be used for coupling on other groups, for example lexitropsin (cf. Example 17; PNA-16). In a similar way, mercaptoalkoxy groups can also be used for further derivatization.

The invention furthermore relates to the use of the PNA derivatives of Formula I as pharmaceuticals. These pharmaceuticals can be used for preventing and/or treating diseases which are accompanied by the expression or overexpression of particular genes. The invention furthermore relates to the use of PNA derivatives as diagnostic agents. These diagnostic agents can be used for diagnosing diseases at an early stage.

When being employed as pharmaceuticals or diagnostic agents, the PNA derivatives of Formula I can be used as antisense agents, anti-gene agents, decoy agents, and chimeraplast agents, depending on their sequence.

The PNA derivatives according to the invention are used, for example, for producing pharmaceuticals for treating diseases in which defined genes are the cause, or are involved, as a result of their overexpression. These pharmaceuticals can, for example, be used for treating diseases which are provoked by viruses, for example by CMV, HIV, HSV-1, HSV-2, influenza, VSV, hepatitis B, or papilloma viruses, with the corresponding virus sequence being the target.

Antisense PNA derivatives according to the invention which are active against these targets have, for example, the following base sequences:

a) against CMV, for example

SEQ ID NO:1      5'-GCGTTTGCTCTTCTTCTTGCG-3' b) against HIV, for example

SEQ ID NO:2      5'-ACACCCAATTCTGAAAATGG-3'
SEQ ID NO:3      5'-AGGTCCCTGTTCGGGCGCCA-3' c) against HSV-1, for example

SEQ ID NO:4      5'-GCGGGGCTCCATGGGGTCG-3'.

Such pharmaceuticals are also suitable, for example, for treating cancer. In this connection, in embodiments, sequences are used which are directed against targets which are responsible for the carcinogenesis or the growth of a cancer, such as by inhibiting telomerase (E. Matthes et al. (1999) Nucleic Acids Res. 27, 1152). Additional targets of this nature include, but are not limited to:
1) Nuclear oncoproteins, such as for example, c-myc, N-myc, c-myb, c-fos, c-fos/jun, PCNA, and p120;
2) Cytoplasmic/membrane-associated oncoproteins, such as for example, EJ-ras, c-Ha-ras, N-ras, rrg, bcl-2, cdc-2, c-raf-1, c-mos, c-src, c-abl, and c-ets;
3) Cell receptors, such as for example, EGF receptor, Her-2, c-erbA, VEGF receptor (KDR-1), retinoid receptors, protein kinase regulatory subunit, c-fms, Tie-2, c-raf-1 kinase, PKC-alpha, and protein kinase A (R1 alpha); and
4) Cytokines, growth factors, and extracellular matrix, such as for example, CSF-1, IL-6, IL-1a, IL-1b, IL-2, IL-4, IL-6, IL-8, bFGF, VEGF, myeloblastin, and fibronectin.

Antisense PNA derivatives which are active against such targets have, for example, the following base sequences:

a) against c-Ha-ras, for example

SEQ ID NO:5       5'-CAGCTGCAACCCAGC-3'
SEQ ID NO:6       5'-TATTCCGTCAT-3'
SEQ ID NO:7       5'-TTCCGTCATCGCTCCTCAGGGG-3' b) bFGF, for example

SEQ ID NO:8       5'-GGCTGCCATGGTCCC-3' c) c-myc, for example

SEQ ID NO:9       5'-GGCTGCTGGAGCGGGGCACAC-3'
SEQ ID NO:10      5'-AACGTTGAGGGGCAT-3' d) c-myb, for example

SEQ ID NO:11      5'-GTGCCGGGGTCTTCGGGC-3' e) c-fos, for example

SEQ ID NO:12      5'-CGAGAACATCATCGTGG-3'
SEQ ID NO:13      5'-GGAGAACATCATGGTCGAAAG-3'
SEQ ID NO:14      5'-CCCGAGAACATCATGGTCGAAG-3'
SEQ ID NO:15      5'-GGGGAAAGCCCGGCAAGGGG-3' f) p120, for example

SEQ ID NO:16      5'-CACCCGCCTTGGCCTCCCAC-3' g) EGE receptor, for example

SEQ ID NO:17      5'-GGGACTCCGGCGCAGCGC-3'
SEQ ID NO:18      6'-GGCAAACTTTCTTTTCCTCC-3' h) p53 tumor suppressor, for example

SEQ ID NO:19      5'-GGGAAGGAGGAGGATGAGG-3'
SEQ ID NO:20      5'-GGCAGTCATCCAGCTTCGGAG-3' i) bcl-2, for example

SEQ ID NO:21      5'-TCTCCCAGCGTGCGCCAT-3' j) VEGF, for example

SEQ ID NO:22      5'-GCGCTGATAGACATCCATG-3'
SEQ ID NO:23      5'-GGAGGCCCGACC-3'
SEQ ID NO:24      5'-GGTTTCGGAGGC-3'
SEQ ID NO:25      5'-TGGTGGAGGTAG-3'
SEQ ID NO:26      5'-GCATGGTGGAGG-3'
SEQ ID NO:27      5'-TTGGCATGGTGG-3'
SEQ ID NO:28      5'-GCCTGGGACCAC-3'
SEQ ID NO:29      5'-CAGCCTGGGACC-3'
SEQ ID NO:30      5'-TGCAGCCTGGGA-3'
SEQ ID NO:31      5'-GTGCAGCCTGGG-3'
SEQ ID NO:32      5'-GGTGCAGCCTGG-3'
SEQ ID NO:33      5'-ATGGGTGCAGCC-3'
SEQ ID NO:34      5'-GGCTTGAAGATG-3'
SEQ ID NO:35      5'-GCAGCCCCCGCA-3'
SEQ ID NO:36      5'-GCAGCAGCCCCC-3' k) c-raf kinase, for example

SEQ ID NO:37      5'-TCCCGCCTGTGACATGCATT-3'

I) PKC-alpha, for example

SEQ ID NO:38      5'-GTTCTCGCTGGTGAGTTTCA-3' m) protein kinase A, for example

SEQ ID NO:39      5'-GCGTGCCTCCTCACTGGC-3'.

Pharmaceuticals comprising PNA derivatives of Formula I are furthermore suitable, for example, for treating diseases which are effected by integrins or cell-cell adhesion receptors, for example by VLA-4, VLA-2, ICAM, VCAM, or ELAM.

Antisense PNA derivatives which are active against such targets have, for example, the following base sequences:

a) VLA-4, for example

SEQ ID NO:40      5'-GCAGTAAGCATCCATATC-3' b) ICAM-1, for example

SEQ ID NO:41      5'-GCCCAAGCTGGCATCCGTCA-3'
SEQ ID NO:42      5'-CCCCCACCACTTCCCCTCTC-3'
SEQ ID NO:43      5'-CTCCCCCACCACTTCCCCTC-3'
SEQ ID NO:44      5'-GCTGGGAGCCATAGCGAGG-3' c) ELAM-1, for example
SEQ ID NO:45      5'-ACTGCTGCCTCTTGTCTCAGG-3'
SEQ ID NO:46      5'-CAATCAATGACTTCAAGAGTTC-3' d) Integrin alpha(V), for example for example

SEQ ID NO:47      5'-GCGGCGGAAAAGCCATCG-3'.

Pharmaceuticals comprising PNA derivatives of Formula I are also suitable, for example, for preventing restenosis. In this connection, it is possible to use PNA sequences which are directed against targets which are responsible for proliferation or migration. Examples of such targets are:
1) Nuclear transactivator proteins and cyclins, such as for example c-myc, c-myb, c-fos, c-fos/jun, cyclins, and cdc2 kinase;
2) Mitogens or growth factors, such as for example PDGF, bFGF, VEGF, EGF, HB-EGF, and TGF-β; and
3) Cell receptors, such as for example bFGF receptor, EGF receptor, and PDGF receptor.

Antisense PNA derivatives which are active against such targets have, for example, the following base sequences:

a) c-myb, for example

SEQ ID NO:48      5'-GTGTCGGGGTCTCCGGGC-3' b) c-myc, for example

SEQ ID NO:49      5'-CACGTTGAGGGGCAT-3' c) cdc2 kinase, for example

SEQ ID NO:50      5'-GTCTTCCATAGTTACTCA-3' d) PCNA (proliferating cell nuclear antigen of rat), for example

SEQ ID NO:51      5'-GATCAGGCGTGCCTCAAA-3'.

PNA derivatives can likewise be used for treating vitiligo and other depigmentation diseases or depigmentation disturbances (e.g. of the skin, the hair, and the eyes), such as albinism and psoriasis, or for treating asthma, with expression of the adenosine A1 receptor, the adenosine A3 receptor or the bradykinin receptor, or of IL-13, being inhibited using suitable antisense agents. An example of such a base sequence is:

SEQ ID NO:52      5'-GATGGAGGGCGGCATGGCGGG-3'.

Pharmaceuticals that comprise a PNA derivative of Formula I can be used, for example, in the form of pharmaceutical preparations which can be administered orally, for example in the form of tablets, coated tablets, hard or soft gelatin capsules, solutions, emulsions, or suspensions. They can also be administered rectally, e.g. in the form of suppositories, or parenterally, e.g. in the form of solutions for injection. In order to produce pharmaceutical preparations, these compounds can be processed in therapeutically inert organic and inorganic excipients. Examples of such excipients for tablets, coated tablets and hard gelatin capsules are lactose, cornstarch or derivatives thereof, tallow and stearic acid or salts thereof. Suitable excipients for preparing solutions include, but are not limited to, water, polyols, sucrose, invert sugar, and glucose. Suitable excipients for injection solutions include, but are not limited to, water, alcohols, polyols, glycerol, and vegetable oils. Suitable excipients for suppositories include, but are not limited to, vegetable oils and hydrogenated oils, waxes, fats, and semiliquid polyols. The pharmaceutical preparations can also comprise preservatives, solvents, stabilizers, wetting agents, emulsifiers, sweeteners, dyes, flavorants, salts for altering the osmotic pressure, buffers, coating agents, antioxidants and, where appropriate, other therapeutically active compounds. The identity and amount of excipient, carrier, and/or additive should conform to the practices known to those of skill in the pharmaceutical art. Techniques for preparation of pharmaceuticals according to the present invention are well known to those of skill in the art and are well within the skill of those artisans. Accordingly, the techniques need not be detailed here. Treatment regimens (e.g., number of doses per unit time, length of treatment, etc.) should conform to the practices known to those of skill in the pharmaceutical art.

Administration forms include, but are not limited to, topical applications; local applications, for example using a catheter or by inhalation; injections or infusions; and oral administration. For injection, the PNA derivatives of Formula I are formulated in a liquid solution, such as in a physiologically acceptable buffer (for example Hank's solution or Ringer's solution). However, the oligonucleotides can also be formulated in solid form and dissolved or suspended before use. Suitable doses for systemic administration are from about 0.01 mg/kg to about 50 mg/kg of bodyweight and per day The invention furthermore relates to pharmaceutical preparations which comprise PNA derivatives of Formula I and/or their physiologically tolerated salts in addition to pharmaceutically acceptable excipients and/or additives.

The PNA derivatives of Formula I and/or their physiologically tolerated salts can be administered to animals, including mammals. In embodiments, the mammal is a human. In embodiments, the mammal is a feline, such as a cat, or a canine, such as a dog. In embodiments, the mammal is an equine, such as a horse; an ovine, such as a cow or steer; a porcine, such as a pig; or an ovine, such as a sheep.

In embodiments, the PNA derivatives of Formula I and/or their physiologically acceptable salts are prepared as pharmaceuticals. In embodiments, they are prepared on their own as pharmaceuticals or they are prepared in mixtures with each other as pharmaceuticals. In other embodiments, they are prepared in the form of pharmaceutical preparations which permit topical, percutaneous, parenteral, or enteral use and which comprise, as the active constituent, an effective dose of at least one PNA derivative together with at least one customary, pharmaceutically acceptable excipient and/or additive. The preparations can comprise from about 0.1 to 90% by weight of the therapeutically active compound. A topical application, for example in the form of ointments, lotions, tinctures, emulsions, or suspensions, is suitable for treating skin diseases.

As discussed above, the pharmaceutical preparations are produced in a manner known to those of skill in the art (see, for example, Remington's Pharmaceutical Sciences, Mack Publ. Co., Easton, Pa.), with pharmaceutically inert inorganic and/or organic excipients being used. It is possible, for example, to use lactose, cornstarch and/or derivatives thereof, tallow, stearic acid and/or its salts, etc., for producing pills, tablets, coated tablets, and hard gelatin capsules, among other things. Non-exclusive examples of excipients for soft gelatin capsules and/or suppositories are fats, waxes, semisolid and liquid polyols, natural and/or hydrogenated oils, etc. Suitable excipients for producing solutions and/or syrups are, for example, water, sucrose, invert sugar, glucose, polyols, etc. Suitable excipients for producing solutions for injection include, but are not limited to, water, alcohols, glycerol, polyols, vegetable oils, etc. Suitable excipients for microcapsules, implants and/or rods include, but are not limited to, copolymers consisting of glycolic acid and lactic acid. Liposome formulations which are known to the skilled person (N. Weiner, Drug Develop Ind Pharm 15

(1989) 1523; "Liposome Dermatics, Springer Verlag 1992), for example HVJ liposomes (Hayashi, Gene Therapy 3 (1996) 878) are also suitable. Dermal application can also be effected, for example, using ionophoretic methods and/or using electroporation.

In addition to the active compounds and excipients, a pharmaceutical preparation can also contain additives, such as fillers, extenders, disintegrants, binders, glidants, wetting agents, stabilizers, emulsifiers, preservatives, sweeteners, dyes, flavorants or aromatizing agents, thickeners, diluents, and buffering substances, and, furthermore, solvents and/or solubilizing agents and/or agents for achieving a sustained release effect, and also salts for altering the osmotic pressure, coating agents and/or antioxidants. They can also comprise two or more different PNA derivatives of Formula I and/or their physiologically tolerated salts and also, furthermore, in addition to at least one PNA derivative of Formula I, one or more different therapeutically active substances. The dose can vary within wide limits and is to be adjusted to the individual circumstances in each individual case. As mentioned above, regulating dosage is well within the abilities of those of skill in the art.

The invention furthermore relates to the use of PNA derivatives of Formula I as diagnostic agents, in particular as aids in DNA diagnosis and in molecular biology (see, for example: Peptide Nucleic Acids: Protocols and Applications; Peter E. Nielsen and Michael Egholm (Edit.) Horizon Scientific Press, 1999). In DNA diagnosis, gene probes, also termed DNA probes or hybridization probes, play an important role in the sequence-specific detection of particular genes. In general, a gene probe consists of a recognition sequence and one or more suitable labeling groups (labels). The specificity with which a target sequence in an analytical sample is identified by means of hybridization with a complementary gene probe is determined by the recognition sequence and its chemical structure. This technique can also be applied to PNA. As compared with oligonucleotides having a natural structure, PNA has the advantage that it has a higher affinity for the target sequence and a greater ability to discriminate between bases.

In an embodiment, the PNA are used in a method for detecting a nucleic acid of interest. In the method, the PNA is labeled with a detectable label, wherein the PNA derivative comprises a base sequence that hybridizes with at least one sequence present in the nucleic acid of interest under selected conditions (for example, stringency conditions that permit specific hybridization). The labeled PNA is combined with a sample suspected of containing the nucleic acid of interest under conditions where specific binding of the PNA derivative to the nucleic acids in the sample can occur. Specific binding of the PNA derivative and nucleic acids present in the sample can then be detected using techniques suitable for the label and known to those of skill in the art. Specific binding indicates the presence of the nucleic acid of interest in the sample.

In embodiments, the nucleic acid is a viral nucleic acid. In embodiments, the nucleic acid is a nucleic acid from a microorganism (e.g., a bacterium).

The use of the compounds of Formula I therefore also relates to in-situ hybridization and fluorescence in-situ hybridization (FISH). In-situ hybridization can also be used, for example, for detecting microorganisms and viruses (Just et al. (1998) J. Vir. Method. 73, 163–174).

Another application of the compounds of the invention relates to detecting and quantifying nucleic acids. Methods for performing such assays can follow along the steps provided above, with the additional step of quantifying the detected nucleic acid using techniques known to those of skill in the art, for example, comparison to concentration standard curves, extrapolation based on extinction coefficients, etc. In addition, for quantitation, use can be made of array technology (Strother et al. J. Am. Chem. Soc. (2000) 122, 1205–1209; Niemeyer et al., Angew. Chem. (1999) 111, 3039–3043; Pirrung (1997) Chem. Rev. 97, 473–488), which provides high sample throughput and a high degree of sensitivity. In embodiments, the PNA probes are fixed on a suitable support or PNA chip. To achieve this, PNA can be synthesized as described in the examples and subsequently fixed onto the support or PNA chip. Alternatively, the PNA can be prepared directly on the support. Another application is the use of the compounds of Formula I as biosensors for detecting nucleic acids (Wang et al (1996) J. Am. Chem. Soc. 118, 7667). The use of PNA of the Formula I possessing an affinity label, such as histidyl-PNA, is another application for purifying nucleic acids (Oerum et al. (1999), in Peptide Nucleic Acids: Protocols and Applications).

The two phosphoryl radicals at the amino terminus and the carboxy terminus can fulfill different functions. For example, the amino terminus can be substituted lipophilically in order to increase the cell uptake, with a fluorescein residue being located at the carboxy terminus for the purpose of detecting the improved cell uptake (cf. PNA-6 in Example 7). Other examples will be apparent to those of skill in the art based on the substituents suitable for inclusion in the PNA derivatives of the invention, as disclosed herein.

The doubly derivatized compounds of Formula I are also suitable for use as so-called "molecular beacons" (Li et al. (2000) Angew. Chemie 112, 1091–1094), which only emit a fluorescence signal in association with binding to a complementary nucleic acid. In these beacons, one end of the PNA, for example the amino terminus, is provided with a fluorescent label whereas the other end, for example the carboxy terminus, is provided with a quencher. The opposite case, in which the N terminus carries a quencher and the C terminus carries a fluorescent label, is also possible. This results in the fluorescence signal being suppressed as long as the doubly labeled PNA derivative does not bind to a complementary nucleic acid. It is only in association with binding that the fluorescent residue (e.g. edans) and the quencher (e.g. dabcyl) become spatially separated from each other, resulting in a fluorescence signal being emitted (Sokol et al. (1998) Proc. Natl. Acad. Sci. 95, 11538).

The PNA backbone can be synthesized using the methods described in the literature, for example using the tert-butyloxycarbonyl(BOC), 9-fluorenylmethoxycarbonyl (Fmoc), or monomethoxytrityl (Mmt) protecting group strategy (Peptide Nucleic Acids: Protocols and Applications; Peter E. Nielsen and Michael Egholm (Edit.) Horizon Scientific Press, 1999). In embodiments, the Mmt protecting group is used for temporarily protecting the amino function of the aminoethylglycine and base-labile protecting groups on the heterocyclic nucleobases (D. Will et al. (1995) Tetrahedron 51,12069; Breipohl et al. (1997) Tetrahedron 53, 14671–14686). Examples of monomeric building blocks are compounds of the Formulae V to V D (below), with A, B, D, E, u' and V' having the meanings defined above. PG can be an amino-protecting group such as benzoyl, anisoyl-, isobutyroyl-, acetyl-, or tert-butylbenzoyl (Breipohl et al. (1997) Tetrahedron 53,14671–14686). TR can be an acid-labile protecting group such as dimethoxytrityl (Dmt) (for V'=O and S) or Mmt (for V'=NH).

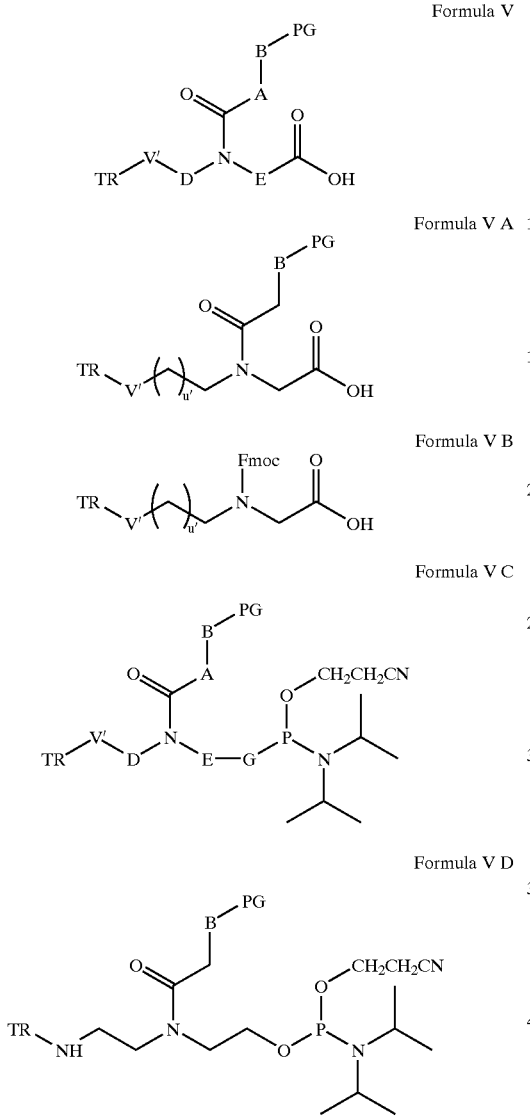

Formula V

Formula V A

Formula V B

Formula V C

Formula V D

After the PNA backbone has been constructed, the free amino function of the N terminus can be reacted directly with an appropriate phosphorylating reagent, for example to give the corresponding phosphoramidate (V'=NR₁ in Formula I).

Figure 6:
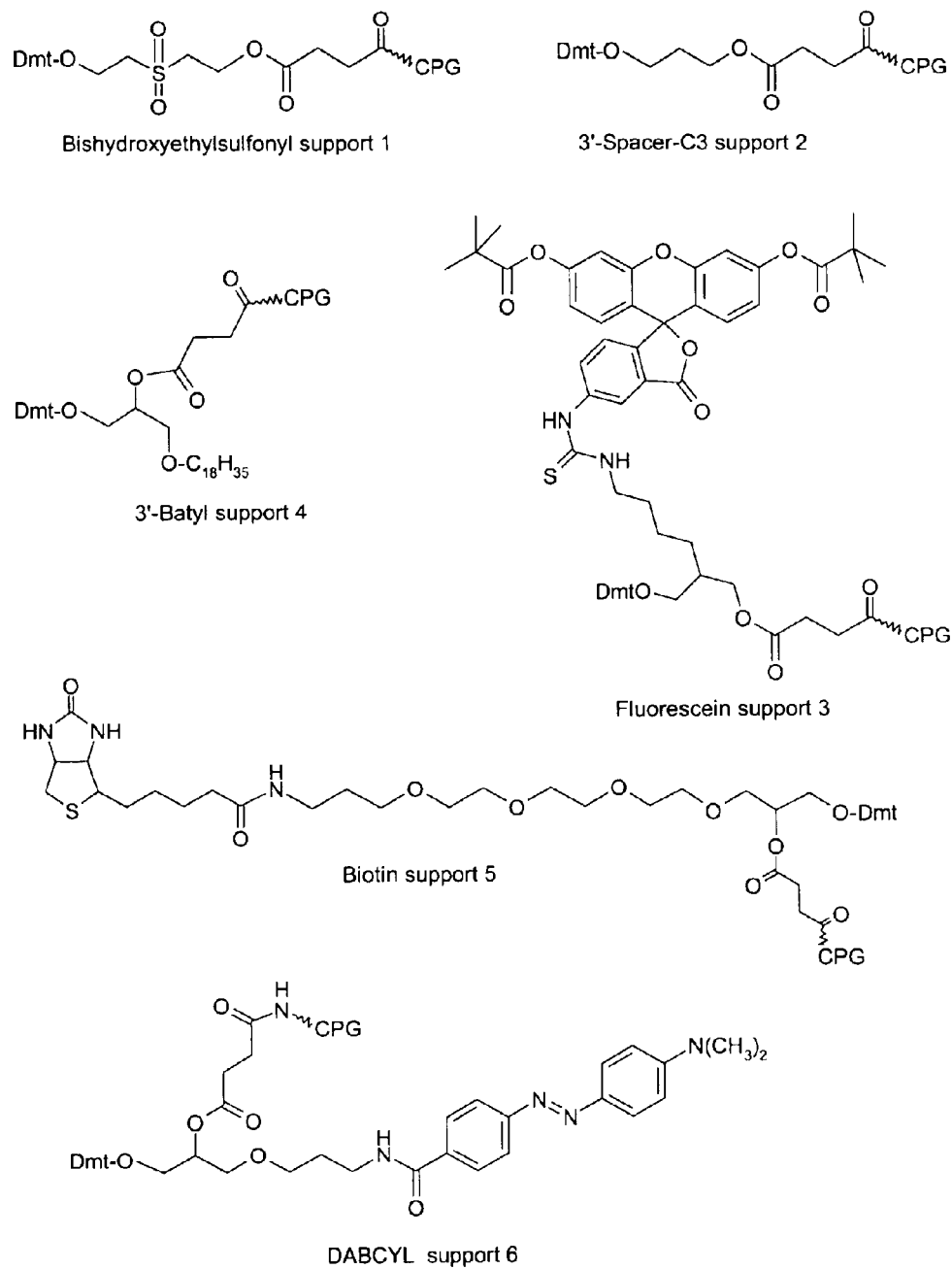
FIG. 6 shows examples of support-bound reagents for solid phase synthesis.

The phosphoryl radicals can be introduced using the reagents which are customarily employed in nucleotide chemistry. There are a large number of phosphorylating reagents available which can be used for preparing the compounds of the Formula I. A non-limiting selection of the reagents is shown in FIGS. 4a to 4d, with the invention not, however, being restricted to these special derivatives. Appropriately modified supports, in particular CPG supports for solid phase synthesis, are used for the carboxy-terminal modification. Non-limiting examples of such supports are listed in FIG. 6.

The phosphorylating reagents employed can be the reagents which are customary in nucleotide chemistry (Glen Research Corporation, Sterling, Va. 20164, U.S.A.; FIGS. 4a to 4d) and which react, for example, in accordance with the phosphoramidite method, the H-phosphonate method or the phosphotriester method (E. Sonveaux (1986) Bioorganic Chemistry 14, 274; S. L. Beaucage and R. P. Iyer (1993) Tetrahedron 49, 1925; E. Uhlmann and A. Peyman (1990) Chem. Rev. 90, 543). The wide variety of possible modifications is determined by the large number of known phosphorylating reagents and appropriately derivatized supports, in particular of controlled pore glass (CPG) supports. TENTAGEL® (from Rapp Polymers GmbH, Tübingen) and aminomethylpolystyrene can be used as solid supports.

In principle, all the reagents which are known in nucleotide chemistry are suitable for introducing the phosphoryl function. Non-exclusive, exemplary reagents are the following reagents of the Formulae VI A, VI B, VI C and VI D

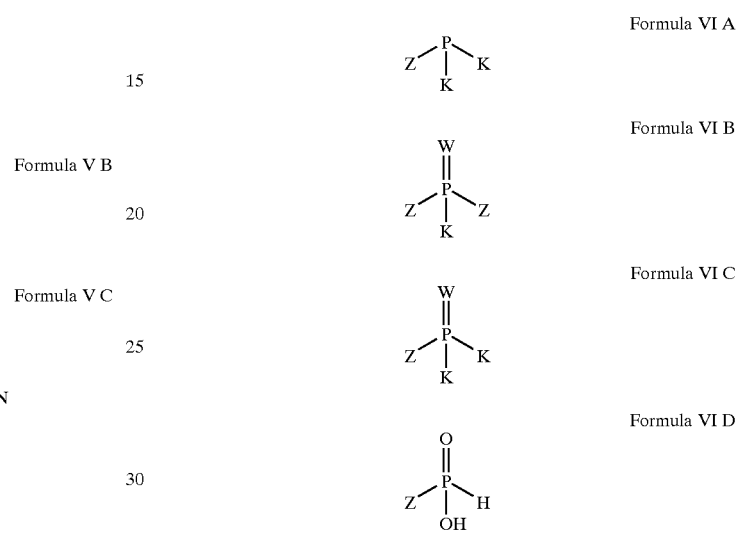

Formula VI A

Formula VI B

Formula VI C

Formula VI D wherein K is halogen (for example, Cl), triazolyl, imidazolyl, or dialkylamino. W can have the above-mentioned meaning or the meaning of W', and Z can have the above-mentioned meaning or the meaning of X, X', or Z', with reactive groups being appropriately protected.

For example, the hydroxyl groups of the fluorescein-phosphoramidite 3 (FIG. 4a) can be protected by esterifying with pivalic acid.

The compounds of Formula VI are only to be regarded as being examples of such reagents, which react, where appropriate, in the added presence of other auxiliary reagents such as bases, acids, or condensing reagents. In embodiments, the reagents of Formula VI A are those which react in accordance with the phosphoramidite method (Beaucage and Iyer, 1993). These reagents are reacted as the phosphorus (III) compound and subsequently oxidized. If, for example, the oxidation is carried out using iodine/water/pyridine or tert-butyl hydroperoxide, the phosphoryl derivatives (W=O) are then obtained. If, on the other hand, the oxidation is carried out using elemental sulfur or Beaucage reagent, the corresponding thiophosphoryl compound (W=S) is then obtained.

Among the reagents (FIGS. 4a to 4d), are also to be found "bifunctional reagents" which, because of the possession of a second function, which is initially protected, can be caused to react several times. The phosphoramidites 4, 6, and 8 to 13 are examples of such bifunctional reagents. In this connection, it can be a matter of the multiple conjugation of a reagent or else of successive reaction with different reagents. Thus, for example, the fluorescein-phosphoramidite 3 can only be caused to react once. By comparison, the fluorescein-phosphoramidite 4 possesses a Dmt group-protected hydroxyl function which can be reacted once again with a phosphorylating reagent after the Dmt group has been eliminated. In this way, it is possible to introduce one and the same group or else different groups several times. PNA-6 is an example of a multiple conjugation at the carboxy terminus and an additional modification at the amino terminus. The fluoroscein and the amino linker were firstly synthesized successively at the carboxy terminus. After the PNA moiety had been synthesized, a hydroxyethylglycine-t building block was coupled on, in the last cycle, with this building block being reacted with C16-phosphorylating reagent 7. PNA-1 and PNA-2 are compounds of Formula I which are only modified with a phosphoryl radical at the carboxy terminus (q=0). This substance class is likewise novel and part of the subject matter of the invention.

Figure 5A:
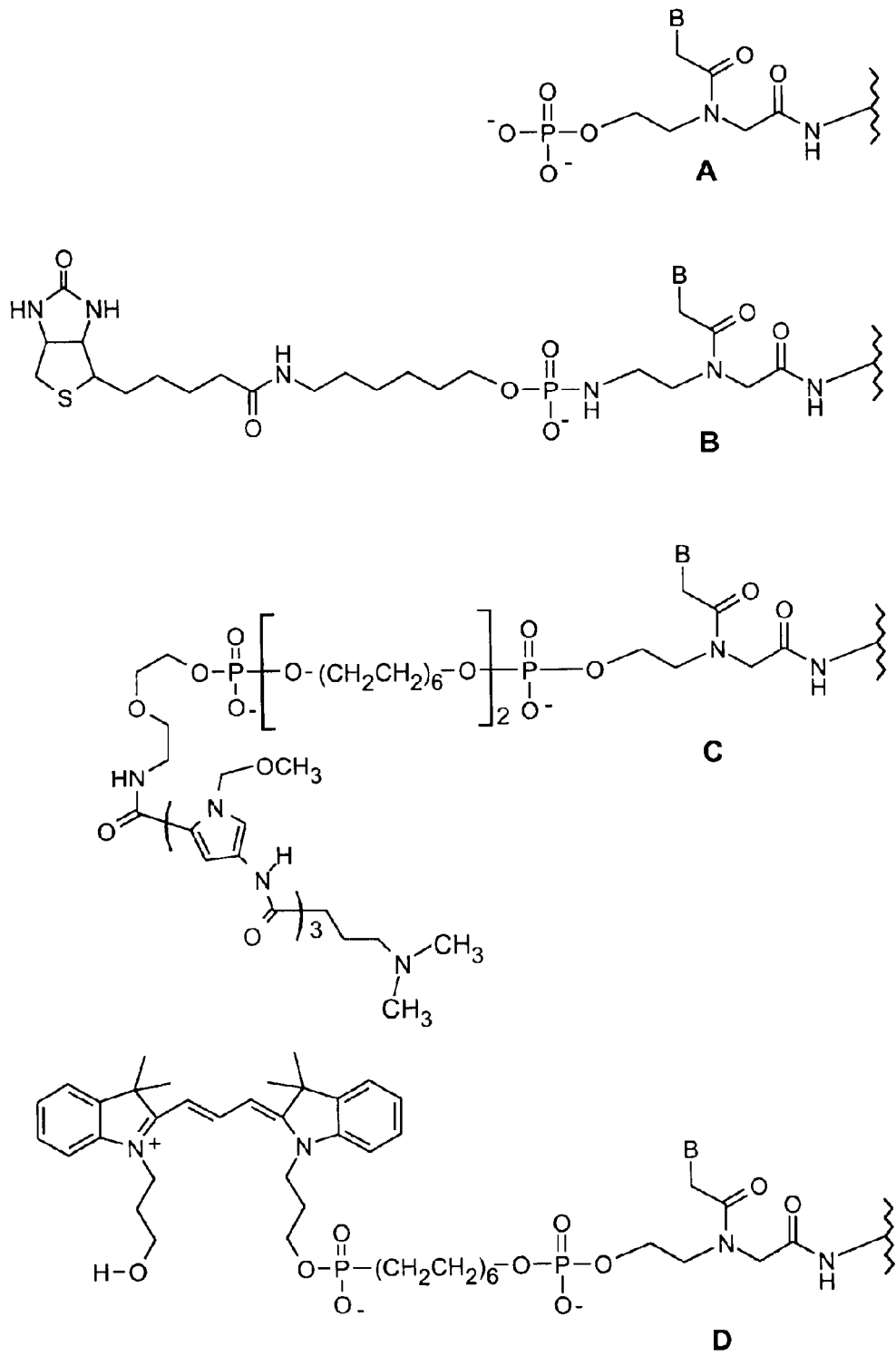
FIGS. 5a and 5b show examples of single (A, B) and multiple (C to E) derivatization of PNA at the N terminus.
Figure 5B:
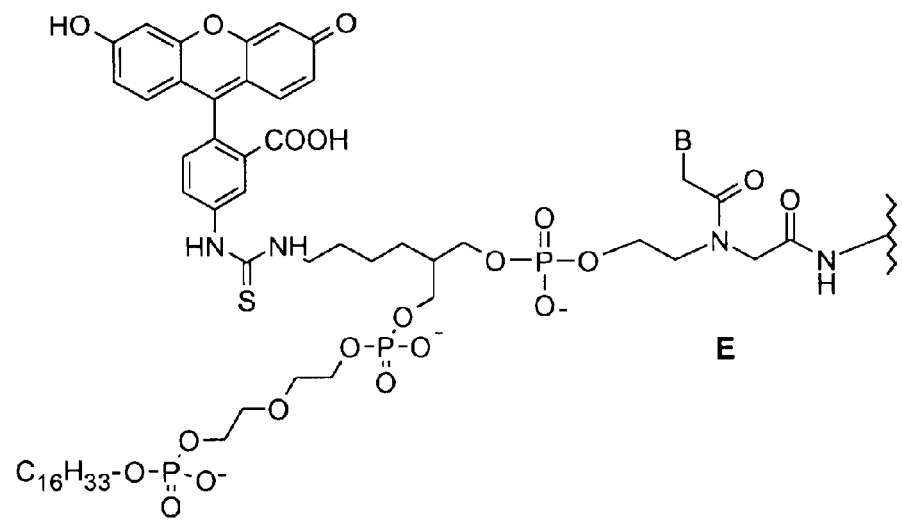
Figure 5B:
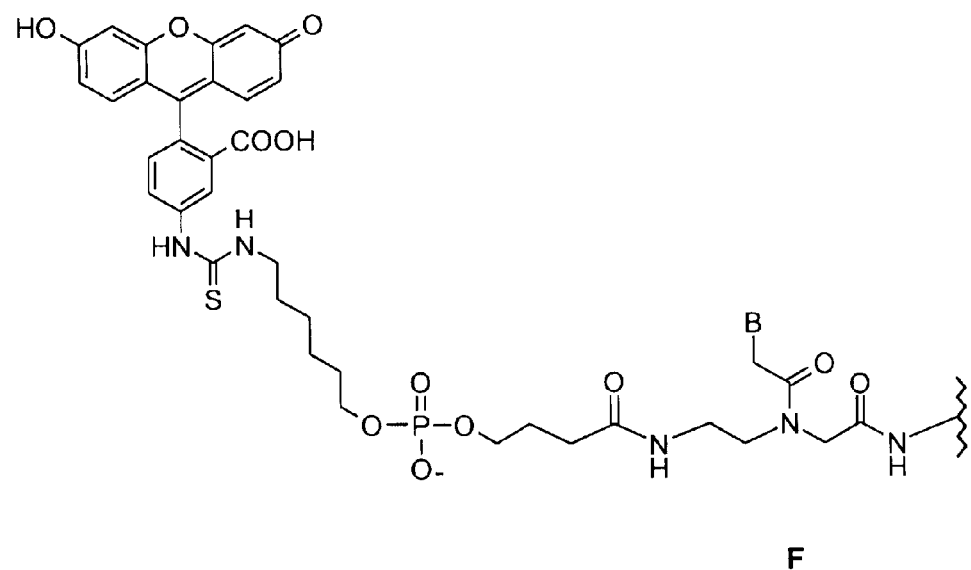

FIGS. 5a and 5b show some examples of compound types for the N-terminal modification of the compounds of Formula I. Compound type A is obtained by reacting the terminal hydroxyl group of the PNA with the phosphorylation reagent 1. Compound type B is obtained by reacting the terminal amino group of the PNA with the biotin-phosphoramidite 5. Compound type C is obtained by successively reacting the PNA having a terminal hydroxyl group with the spacer-18 phosphoramidite 9, amino modifier-5 phosphoramidite 12 and lexitropsin. Compound type D is obtained by successively reacting the PNA having a terminal hydroxyl group with the spacer-9 phosphoramidite 8 and the cyanine-3 phosphoramidite 10. Compound type E is obtained by successively reacting the PNA having a terminal hydroxyl group with the bifunctional fluorescein-phosphoramidite 4, the spacer-9 phosphoramidite 8, and the C16-phosphorylating reagent 7. The steps which additionally have to be carried out, such as oxidation and protecting group elimination, are described in the examples.

Figure 7:
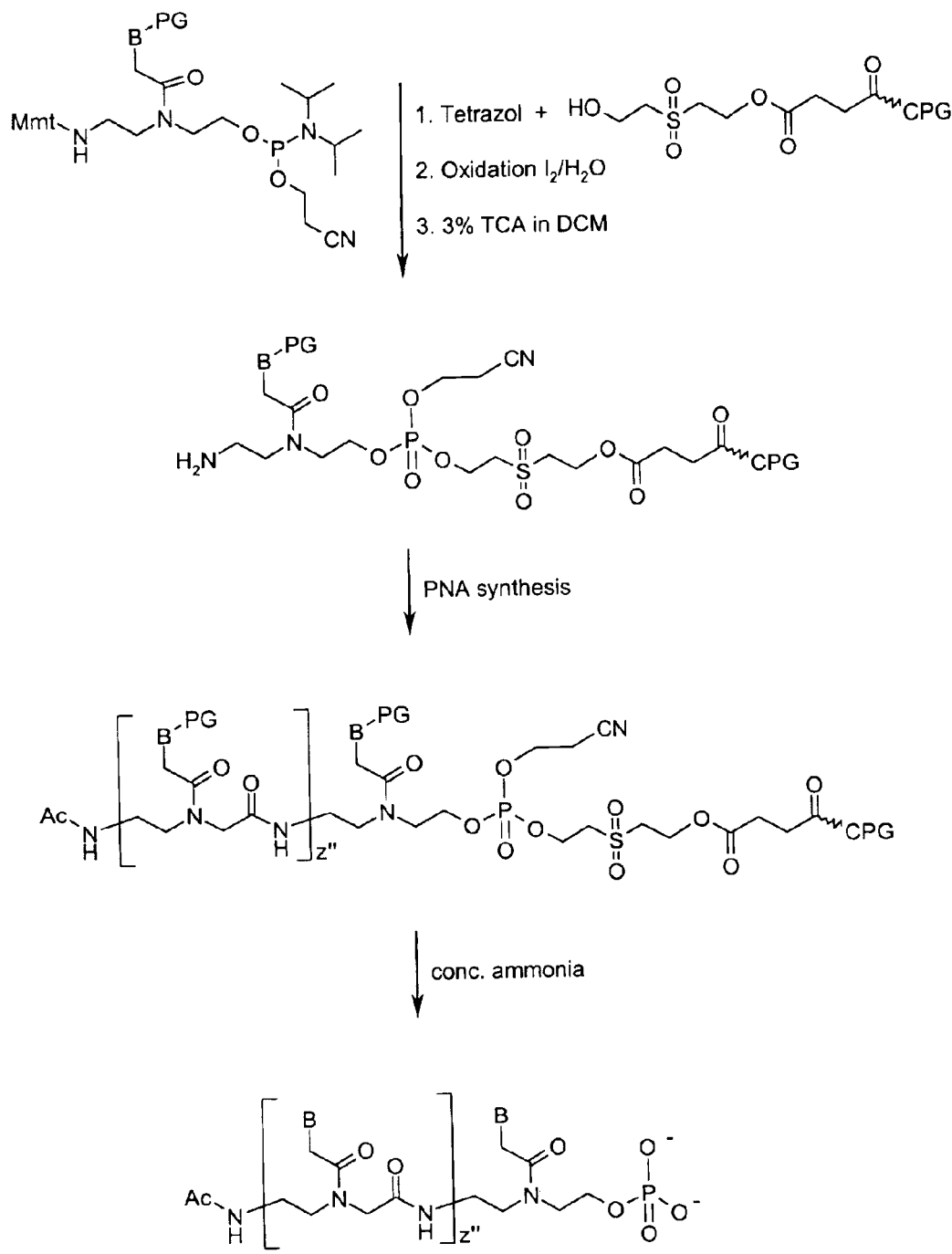
FIGS. 7, 8 and 9 show examples of synthesizing C-and N-terminally modified PNA.
Figure 8:
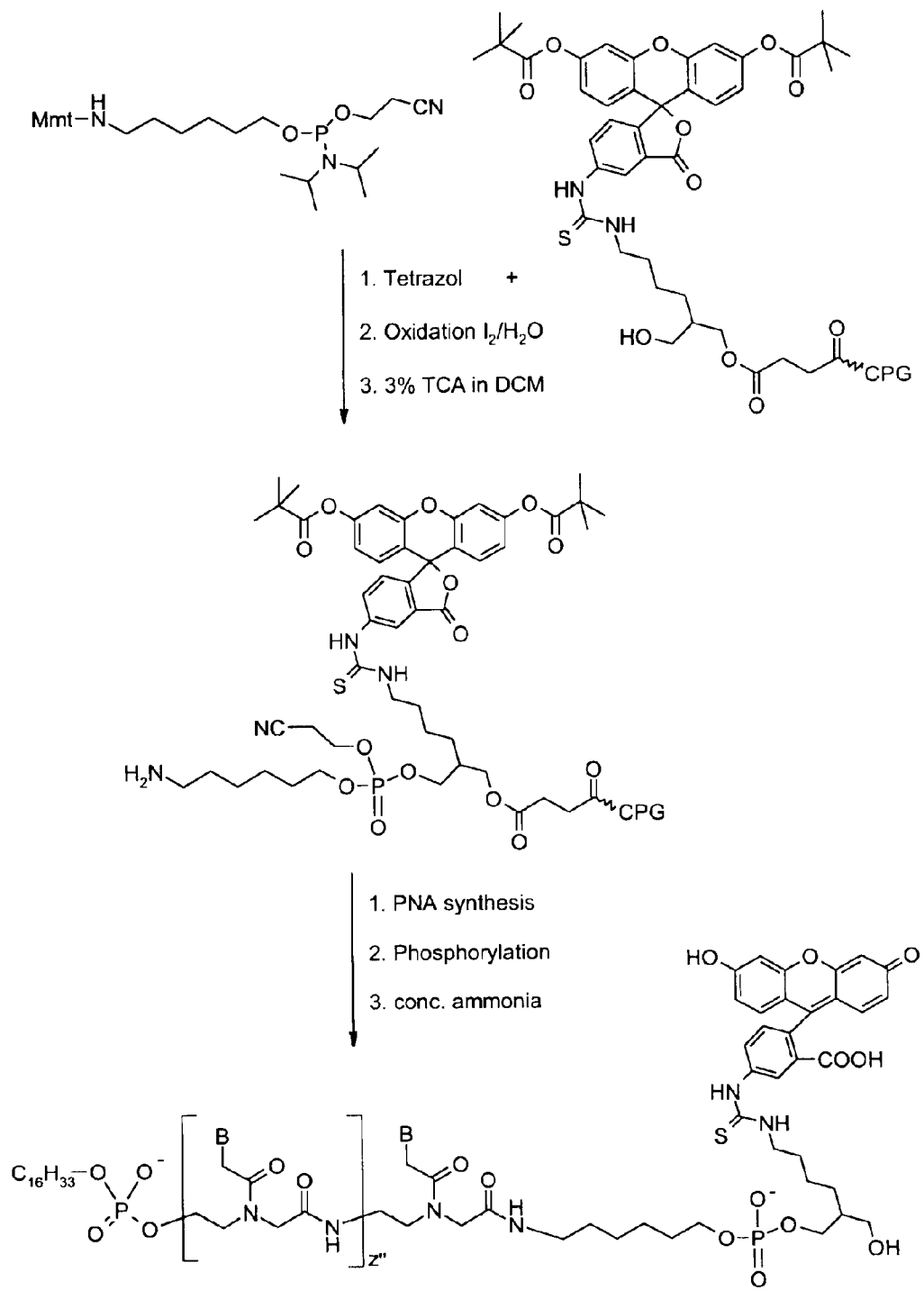

An example of a carboxy-terminal modification of PNA obtained using a phosphoramidite of the Formula V D is depicted in FIG. 7. In this case, the starting material is a bishydroxyethylsulfone support I (FIG. 6), which, after the Dmt group has been eliminated with 3% trichloroacetic acid, is reacted with the phosphoramidite of the Formula V D using tetrazole as catalyst. After oxidizing with iodine water, the amino-terminal Mmt group is eliminated with 3% trichloroacetic acid and the PNA moiety is then synthesized using methods known from the literature, for example using the Mmt method which is explained below. An alternative method for the carboxy-terminal modification uses CPG supports which are modified in accordance with the radical to be introduced, and consequently contain the fluorescein radical, for example (FIG. 8). This method will be explained using the example of a PNA derivative which is modified amino-terminally with a hexadecyl phosphate radical and carboxyterminally with a fluorescein phosphate. The fluorescein support 3 (FIG. 6) is first of all detritylated with trichloroacetic acid and then condensed with the amino modifier C6 phosphoramidite 13 (FIG. 4d) using tetrazole.

Figure 9:
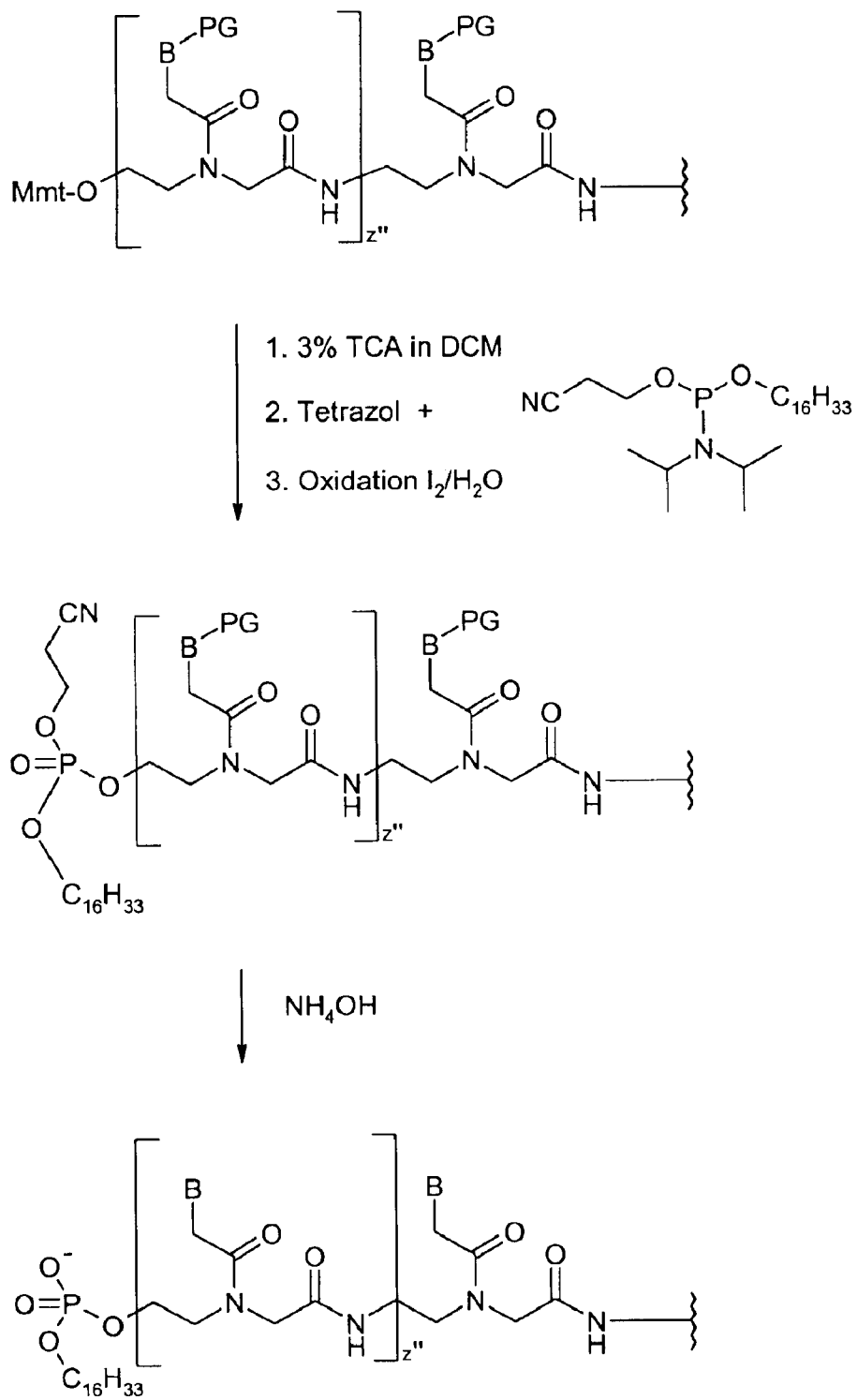

After oxidizing with iodine water and eliminating the Mmt group, the PNA moiety can be synthesized using customary methods. In the last cycle, a hydroxyethylglycine-based PNA building block (Formula V A, u'=2, V'=oxygen) is coupled on, with this building block being reacted as shown in FIG. 9 after eliminating the Dmt protecting group using the C16 phosphorylating reagent 7. The doubly modified PNA derivative is obtained after eliminating all the protecting groups and cleaving from the CPG support.

In embodiments, the invention provides a process for preparing a PNA derivative of Formula I in which q is 0. In these embodiments, the process comprises linking the C-terminus of an amidonucleic acid, which is optionally N-terminally protected, to a solid phase-bound phosphorylating reagent, or binding an amidonucleic acid which is phosphorylated C-terminally to a solid support. Optionally, the backbone of the PNA oligomer is then extended by sequentially coupling with amidonucleic acid monomers. Optionally, the N-terminus of the PNA oligomer is then deprotected. In embodiments, the PNA is prepared using t-butyloxycarbonyl (BOC), 9-fluorenylmethoxycarbonyl (Fmoc), or monomethoxytrityl (Mmt) protecting groups.

In embodiments, the invention provides a process for preparing a PNA derivative of Formula I in which q is 1, wherein the process comprises:

a) linking the C-terminus of an amidonucleic acid, which is optionally N-terminally protected, to a solid phase-bound phosphorylating reagent, or binding an amidonucleic acid which is phosphorylated C-terminally to a solid support, b) optionally, extending the backbone of the PNA oligomer by sequentially coupling with amidonucleic acid monomers, c) optionally, deprotecting the N-terminally protected PNA backbone, d) coupling a phosphorus (III) or a phosphorus (IV) group to the N-terminus of the PNA backbone using activated phosphorylating reagents optionally containing a spacer, e) optionally, repeating step d), and f) optionally, oxidizing the phosphorus (III) group to a phosphorus (V) group.

EXAMPLES

The following examples are presented to more fully describe selected embodiments of the invention. The following examples are not intended, and should not be construed, to limit the invention in any way.

The preparation of the following compounds is described by way of example:

PNA-1:

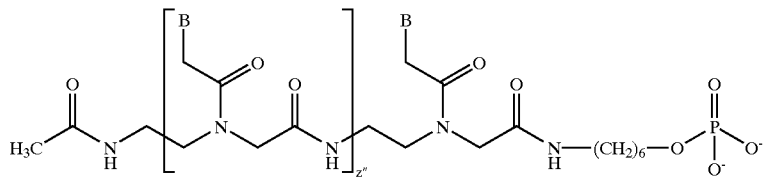

PNA-2:
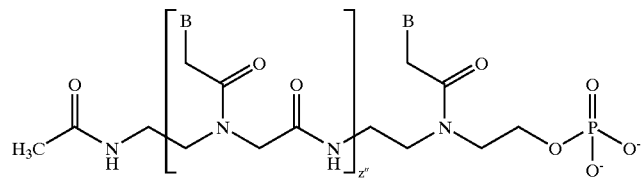
PNA-3:
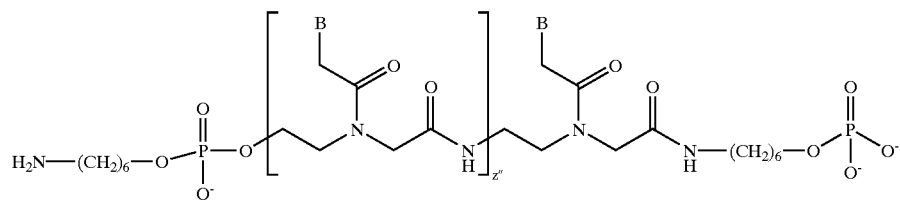
PNA-4:
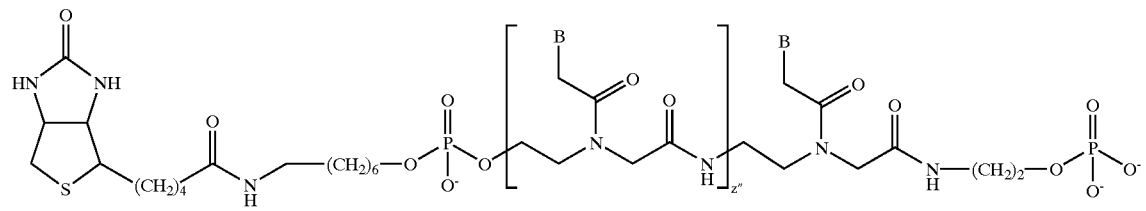
PNA-5:
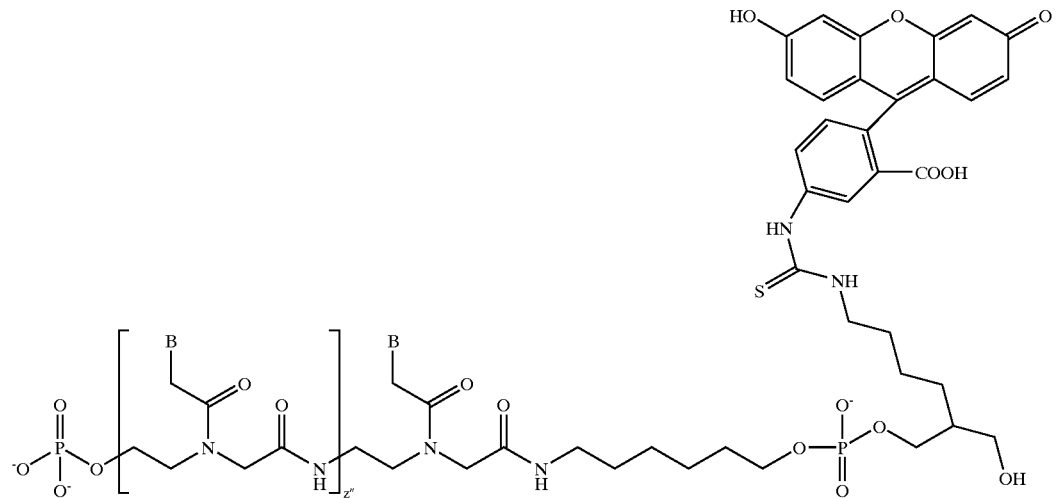

PNA-6:

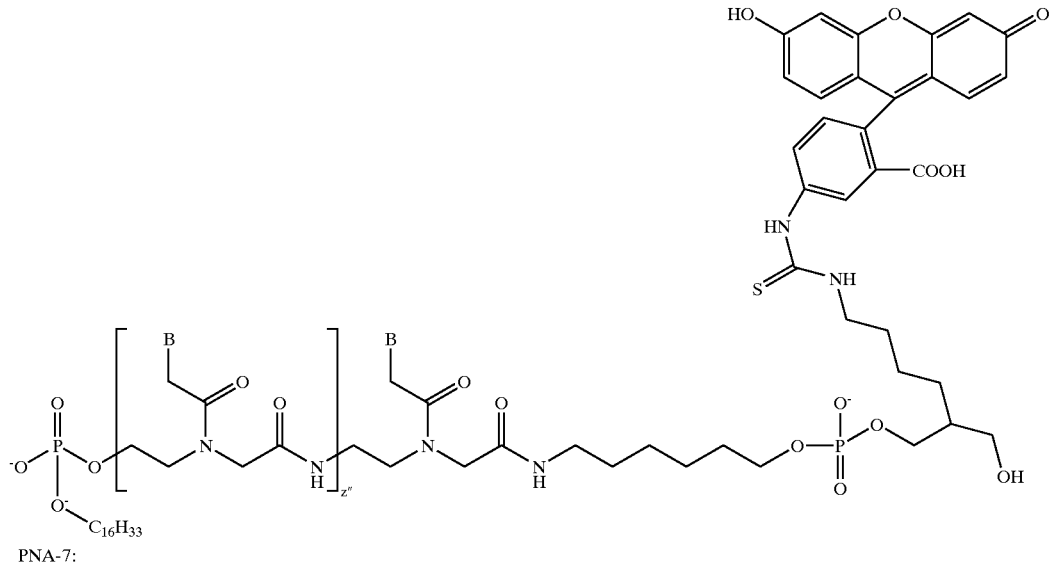

PNA-7:

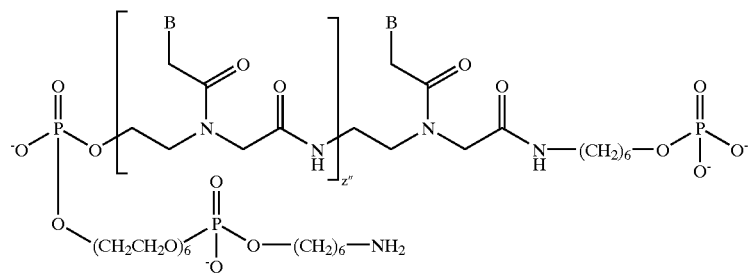

wherein the sequences of the 13 bases are in each case described by SEQ ID NO:53, and z" in each case is 10:

SEQ ID NO:53    5'-TATTCCGTCAT-3'

Example 1

Synthesizing the PNA Chain

The following reagents were used for preparing the PNA moiety:

1. Phosphoramidite reagent (0.1 M in acetonitrile (ACN))
2. Mmt-PNA monomers and/or Dmt-oeg-PNA monomers (0.2 M in DMF:ACN (1:1; v:v))
3. Anhydrous ACN (≦30 ppm of water)
4. Trichloroacetic acid (3%) in dichloromethane (DCM)
5. Acetic anhydride, 2,6-lutidine in THF (1:1:8; v:v:v); (Cap A)
6. N-Methylimidazole (16%) in THF; (Cap B)
7. Iodine solution (0.05 M) in THF, water, pyridine (7:2:1; v:v:v)
8. Washing solution (THF, water, pyridine (7:2:1; v:v:v))
9. Tetrazole (0.3 M) in ACN
10. HBTU; 0.2 M in DMF:ACN (1:1; v:v)
11. DIPEA; 0.2 M in DMF:ACN (1:1; v:v)
12. DMF (>99.5%)
13. Solid phase support: aminopropyl-CPG (550 A) loaded with Mmt-aminohex-1-yl hemisuccinate (for PNA-hexylamides).

The Mmt/acyl-protected or Dmt/acyl-protected oeg monomers were prepared as has already been described (Breipohl et al. (1997) Tetrahedron 53, 14671–14686). The loading of aminopropyl-CPG with the Mmt-aminohex-1-yl hemisuccinate has likewise already been described (Will et al. (1995) Tetrahedron 51, 12069–12082). The derivatized CPG supports are commercially available (Glen Research Corporation, Sterling, Va. 20164, U.S.A.). The PNA syntheses were in general carried out on a scale of from 2 to 5 μmol.

The following cycle was used for the PNA synthesis:

1. Step of washing with ACN
2. Deprotecting the Mmt group or the Dmt group by treating with 3% trichloroacetic acid (TCA) in DCM; 110 sec.
3. Step of washing with DMF/ACN (1:1)
4. Neutralizing with DIPEA in DMF/ACN (1:1)
5. Coupling on the monomeric building block by preactivating (15 min) with HBTU/DIPEA/PNA monomer (ratio 1:1:1; total volume 450 μl) charging the solid phase and coupling (45 min)
6. Step of washing with ACN
7. Capping with acetic anhydride/N-methylimidazole
8. Step of washing with ACN
9. New cycle

Example 2

Synthesizing acetyl-tat tcc gtc at-aminohexyl-p (PNA-1)

The Dmt protecting group was first of all eliminated from the bishydroxyethylsulfonyl support 1 (1 μmol, FIG. 6) by treating with 3% trichloroacetic acid. The free hydroxyl function was then reacted with the amino modifier C6 phosphoramidite 13 (FIG. 4d) using tetrazole as catalyst. The reaction employs an excess of the phosphorylating reagent 13 (approx. 25-fold), as an 0.3 M solution in acetonitrile/tetrahydrofuran (1:1; v:v), and the tetrazole (approx. 50-fold; 0.5 M in acetonitrile). After the condensation took place, oxidation was effected using an iodine solution (0.05 M in tetrahydrofuran/water, pyridine (7:2:1; v:v:v)). After that, the PNA moiety was prepared by solid phase synthesis as described in Example 1. In the last cycle, the free amino function was acetylated by treating with the capping reagent. This prevented the PNA from being degraded amino-terminally during deprotection with conc. ammonia. Finally, the PNA was cleaved from the support, and the protecting groups were removed at the same time, by treating with conc. ammonia at 50° C. overnight. 103 OD (260 nm) of the desired crude product was obtained. The crude product was purified by preparative polyacrylamide (PAA) gel electrophoresis. The desired product band was eluted with 0.2 M triethylammonium bicarbonate buffer and desalted through a Bond-Elute C18 column (1 g). 23.3 OD was obtained. The product was analyzed by negative ion mass spectrometry, which confirmed the calculated mass (calc. 3166.2; found 3166.8).

Example 3

Synthesizing acetyl-tat tcc gtc at(eo)-p (PNA-2)

The preparation was effected, in a 1 μmol synthesis, in an analogous manner to that described in Example 2. After the Dmt protecting group was eliminated from the support (FIG. 6), the free hydroxyl function was reacted with the phosphoramidite of Formula V D using tetrazole as catalyst. The reaction employs an excess of the phosphoramidite (approx. 20-fold), as a 0.1 M solution in acetonitrile/tetrahydrofuran (1:1; v:v) and the tetrazole (approx. 50-fold; 0.5 M in acetonitrile). After the condensation took place, oxidation was effected using an iodine solution (0.05 M in tetrahydrofuran/water, pyridine (7:2:1; v:v:v)). 50 OD of crude product was obtained after cleaving with ammonia. 45 OD of this crude product was purified by electrophoresis through a 15% PAA gel. 13.2 OD of product, having a molecular weight of 3052.9 (calc. 3052.9), was obtained.

Example 4

Synthesizing aminohexyl-p-t(oeg) at tcc gtc at-aminohexyl-p (PNA-3)

The preparation was effected, in a 1 μmol synthesis, in an analogous manner to that described in Example 2. However, after the carboxy terminus and the PNA moiety had been synthesized, a hydroxyethylglycine-based building block having thymine as the nucleobase (oegT) was coupled on in the last cycle. After the Dmt group was eliminated, the free hydroxyl function was coupled to the amino modifier C6 phosphoramidite 13 (FIG. 4d) using tetrazole as catalyst and subsequently oxidized with iodine water. The oligomer was cleaved from the support, and all the base-labile protecting groups were removed at the same time, by treating with conc. ammonia at 50° C. The terminal Mint protecting group was then removed by treating with 80% acetic acid. 130 OD of the crude product was obtained, with this group product being purified by gel electrophoresis. 22.5 OD of product, having a molecular weight of 3303.8 (calc. 3305.0), was obtained.

Example 5

Synthesizing biotin-p-t(oeg) at tcc gtc at-aminohexyl-p (PNA-4)

The preparation was effected, in a 0.5 μmol synthesis, in an analogous manner to that described in Example 2. However, after synthesizing the carboxy terminus and the PNA moiety, a hydroxyethylglycine-based building block having thymine as the nucleobase (oegT) was coupled on in the last cycle. After eliminating the Dmt group, the free hydroxyl function was coupled to the biotin phosphoramidite 5 (FIG. 4b) using tetrazole as catalyst and subsequently oxidized with iodine water and detritylated with trichloroacetic acid. The oligomer was cleaved from the support, and all the protecting groups were removed at the same time, by treating with conc. ammonia at 50° C. 37 OD of the crude product was obtained, with this crude product being purified by gel electrophoresis. 22.5 OD was obtained.

Example 6

Synthesizing p-t(oeg) at tcc gtc at-aminohexyl-p-fluorescein (PNA-5)

The synthesis was effected in analogy with Example 2 proceeding from the fluorescein-support 3 (FIGS. 6a and 8). The Dmt protecting group was eliminated from the fluorescein-support 3 by treating with 3% trichloroacetic acid. The free hydroxyl function was then reacted with the amino modifier C6 phosphoramidite 13 (4d) using tetrazole as catalyst. After condensation had taken place, oxidation was effected using an iodine solution (0.05 M in tetrahydrofuran/water, pyridine (7:2:1; v:v:v)). After that, the PNA moiety was prepared by solid phase synthesis as described in Example 1. A hydroxyethylglycine-based building block having thymine as nucleobase ((t)oeg) was coupled on in the last cycle. After eliminating the Dmt group, the free hydroxyl function was coupled to the phosphorylating reagent 1 (FIG. 4a) using tetrazole as catalyst and subsequently oxidized with iodine water. Finally, the PNA was cleaved from the support, and the protecting groups were removed at the same time, by treating with conc. ammonia at 50° C. overnight. 61 OD (260) of the crude product was obtained, with this crude product being purified by preparative polyacrylamide (PAA) gel electrophoresis. The desired product band was eluted with 0.2M triethylanimonium bicarbonate buffer and desalted through a Bond-Elut C18 column (1 g). 5.6 OD was obtained. The product was analyzed by negative ion mass spectroscopy, which showed the calculated mass (calc. 3709.5; found 3706.3).

Example 7

Synthesizing C16-p-t(oeg) at tcc gtc at-aminohexyl-p-fluorescein (PNA-6)

The synthesis was effected in analogy with Example 6 starting from 1 μmol of fluorescein support 3 (FIGS. 6a and 8). A hydroxyethylglycine-based building block having thymine as the nucleobase ((t)oeg) was coupled on in the last cycle. However, after eliminating the Dmt group, the free hydroxyl function was coupled to the C16 phosphorylating reagent 7 (FIG. 4c) using tetrazole as catalyst and subsequently oxidized with iodine water. Finally, the PNA was eliminated from the support, and the protecting groups were removed at the same time, by treating with conc. ammonia at 50° C. overnight. 61 OD (260) of the desired crude product was obtained, with this crude product being purified by preparative polyacrylamide (PAA) gel electrophoresis. The desired product band was eluted with 0.2M triethylammonium bicarbonate buffer and desalted through a Bond-Elut C18 column (1 g). 4.6 OD was obtained. The product was analyzed by negative ion mass spectrometry, which showed the calculated mass (calc. 3934, found 3931).

Example 8

Determining the Melting Temperatures

The melting temperatures were determined using an HP 8452A diode-array spectrophotometer, an HP 89090A Peltier element and HP Temperature Control Software Rev. B5.1 (from Hewlett Packard). Measurements were taken in 0.5° C./min steps in 140 mM KCl, 10 mM sodium dihydrogen phosphate, 0.1 mM EDTA (pH 7.4) as the buffer. The oligomer concentration was from 0.5 to 1 $OD_{260}$ per ml.

Surprisingly, the doubly phosphoryl-modified PNA-5 and PNA-6 derivatives having two or three negative charges exhibited an equally good or better degree of binding towards complementary DNA and RNA than did the uncharged PNA (reference substance).

| PNA derivative | | $T_m$ (DNA) | $T_m$ (RNA) |
|---|---|---|---|
| Reference | Ac-HN-tat tcc gtc at-hex | 41.9° C. | 56.6° C. |
| PNA-5 | p-t(oeg) at tcc gtc at-aminohexyl-p-fluorescein | 41.8° C. | 56.9° C. |
| PNA-6 | C16-p-t(oeg) at tcc gtc at-aminohexyl-p-fluorescein | 44.1° C. | 56.9° C. |

Example 9

Determining Cell Uptake After Fluorescence Labeling

COS cells were allowed to grow to confluence in Dulbecco's MEM, which was supplemented with 10% FCS, in 5 cm Petri dishes. The cells were washed twice with serum-free DMEM. An area of approx. 1 $cm^2$ was scratched out in the middle of the Petri dish using a sterile needle. The PNA solution (10 μM) under investigation was applied in this area. The dish was incubated at 37° C. under a $CO_2$ atmosphere. After 2, 4 and 16 hours, the cells were examined by fluorescence microscopy. For this, the cells were washed four times with serum-free DMEM, covered with a cover slip, and evaluated under the fluorescence microscope or by phase contrast. PNA-5 and PNA-6 were examined by fluorescence microscopy.

In this connection, it was found that the hexadecyl-PNA derivative (PNA-6) was taken up more efficiently into the cells than the PNA with no hexadecyl radical.

Example 10

Inhibiting Cell Proliferation with PNA-6

The sequence of PNA-6 is directed against the translation start of the Ha-ras mRNA. REH cells (human pre-B leukemia cells, DSM ACC 22) or A549 tumor cells were cultured, at 37° C. and under 5% $CO_2$, in OptiMEM (Gibco BRL) containing 10% fetal calf serum (FCS, GIBCO-BRL). The cell density for the assay was approx. 1×10⁶/ml. The PNA-6 (10 μM) was incubated with the cells in 24-well plates. After incubating at 37° C. and under 5% $CO_2$ for 96 hours, the cell density was determined. Mean values for the cell density were determined from 3 individual wells at a given PNA concentration. It was found that PNA-13 inhibits proliferation of the REH cells. After >4 days of incubation, the inhibition brought about by PNA-6 was greater than that brought about by a corresponding phosphorothioate oligonucleotide.

Example 11

Synthesizing aminohexyl-p-spacer18-p-t(oeg) at tcc gtc at-aminohexyl-p (PNA-7)

The synthesis was effected in a 1 μmol synthesis, in an analogous manner to that described in Example 2. However, after the carboxy terminus and the PNA moiety had been synthesized, a hydroxyethylglycine-based building block having thymine as the nucleobase (oegT) was coupled on in the last cycle. After eliminating the Dmt group, the free hydroxyl function was coupled to the spacer 18 phosphoramidite (FIG. 4c) and, after detritylating once again, to the amino modifier C6 phosphoramidite 13 (FIG. 4d) using tetrazole as catalyst and subsequently oxidized with iodine water. The oligomer was cleaved from the support, and all the base-labile protecting groups were removed at the same time, by treating with conc. ammonia at 50° C. The terminal Mmt protecting group was then removed by treating with 80% acetic acid. 57 OD of the crude product was obtained, with this crude product being purified by gel electrophoresis. 7.4 OD of product, which exhibits the expected molecular weight of 3647.5 (calc. 3648.5) in the mass spectrum, was obtained.

| List of abbreviations: | |
|---|---|
| ACN | Acetonitrile |
| BOC | tert-butyloxycarbonyl |
| C, c | pseudo-iso-cytosine |
| COS | CV1 origin SV 40 |
| CPG | controlled pore glass |
| DCM | Dichloromethane |
| DIPEA | Diisopropylethylamine |
| DMEM | Dulbecco's MEM |
| DMF | Dimethylformamide |
| Dmt | Dimethoxytrityl |
| DNA | deoxyribonucleic acid |
| DNP | Dinitroaryl |
| FITC | fluorescein isothiocyanate |
| Fmoc | Fluorenylmethoxycarbonyl |
| HATU | O-(7-azabenzotriazol-1-yl)-1,1,3,3-tetramethyluronium hexafluorophosphate |
| HBTU | O-(benzotriazol-1-yl)-1,1,3,3-tetramethyluronium hexafluorophosphate |
| Hex | —NH—$(CH_2)_6$—OH |
| MEM | modified Eagle's minimal essential medium |
| Mmt | Monomethoxytrityl |
| OD | optical density |
| Oeg | N-(2-hydroxyethyl)glycine |
| PAA | Polyacrylamide |
| PG | protecting group |
| PNA | polyamide nucleic acid |
| RNA | ribonucleic acid |
| TBTU | O-(benzotriazol-1-yl)-1,1,3,3-tetramethyluronium tetrafluoroborate |
| TCA | trichloroacetic acid |
| THF | Tetrahydrofuran |
| TR | acid-labile protecting group |

All references cited herein are hereby incorporated in their entirety by reference.

What is claimed is:

1. A PNA derivative which carries one or more phosphoryl radicals at the C terminus or at the C and N termini of the PNA backbone, wherein the one or more phosphoryl radicals are selected from oxo-, thio-, and imino-phosphoryl radicals, and wherein at least one of the phosphoryl radicals carries one or more deprotonatable groups, and wherein the phosphoryl radicals are linked to the PNA backbone by way of an oxygen-phosphorus bond, a sulfur-phosphorus bond or a nitrogen-phosphorus bond, either directly or by way of a spacer.

2. A PNA derivative as claimed in claim 1, wherein the spacer is an alkanoylamide, a poly(alkoxy)carboxamide, or an amino acid.

3. A PNA derivative of Formula I

Formula I

[structure: N terminus ... C terminus with W', W, P, X', X, Y', Y, Z', Z, V', V, D', {POLY}, subscripts n, q, 1-q, m]

N terminus        C terminus wherein
  q is 0 or 1;
  D' is, independently of each other, hydroxyl, mercapto, amino, alkylamino, or acylamino;
  V is oxygen, sulfur, or $NR_1$;
  V' is, independently of any other V', oxygen, sulfur, $NR_1$, $U-(CR_3R_4)_{u'}-C(O)-NH$, or $U-(CH_2CH_2O)_{u'}-CH_2-C(O)-NH$;
  U is, independently of any other U, oxygen, sulfur, or NH;
  u' is, independently of any other u', from 1 to 10;
  W and W' are, independently of each other, oxygen, sulfur, or $NR_1$;
  Y and Y' are, independently of each other, hydroxyl, mercapto, oxyanion, thioate, or $NR_1R_2$;
  X and X' are, independently of each other,
    $U-(C_2-C_{22}$-alkanediyl$)$-U,
    $U-(CH_2CH_2-O)_{u'}$,
    a labeling group,
    a group for crosslinking,
    a group which promotes intracellular uptake, or
    a group which increases the binding affinity of the PNA derivative for nucleic acids;
  Z and Z' are, independently of each other,
    hydroxyl,
    mercapto,
    oxyanion,
    thioate,
    $NR_1R_2$,
    $C_1-C_{22}$-alkyl,
    $C_1-C_8$-arylalkyl,
    $C_1-C_{22}$-alkyl-U,
    $C_1-C_8$-arylalkyl-U,
    hydroxy-$C_1-C_{18}$—U,
    aminoalkyl-U,
    mercaptoalkyl-U,
    a group of the formula $R_7(CH_2CH_2-O)_{m'}$, wherein $R_7$ is hydroxyl, amino, or $C_1-C_{22}$-alkoxy, and m' is from 1 to 100,
    a labeling group,
    a crosslinking group,
    a group which promotes intracellular uptake, or
    a group which increases the binding affinity of the PNA derivative for nucleic acids;
  $R_1$ and $R_2$ are, independently of each other, a radical consisting of hydrogen or $C_1-C_6$-alkyl, preferably hydrogen,
  $R_3$ and $R_4$ are, independently of each other, a radical consisting of hydrogen or $C_1-C_6$-alkyl, or the radical of an amino acid side chain, wherein adjacent radicals $R_3$ and $R_4$ in V' can also form a $C_5-C_8$-cycloalkyl ring;
  n is from 0 to 10;
  m is from 0 to 10;

and wherein {POLY} is described by Formula II

Formula II

[structure: {BLOCK}—C(O)—NH—{BLOCK}—G, subscript z'']

wherein {BLOCK} is, independently of any other {BLOCK}, a group selected from

Formula IIIA

[structure with B, A, O, D, N, E]

Formula IIIB,

Formula IIIB

[structure with H, N, D, E]

and Formulae IV A TO IV G,

Formula IV A

[structure with B, O, N]

Formula IV

[structure with B, O, N, $R_3$]

Formula IV C

[structure with B, O, N]

Formula IV D

[structure with B, N]

Formula IV E

[structure with B, H]

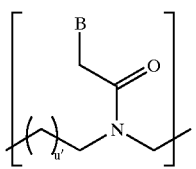

Formula IV F

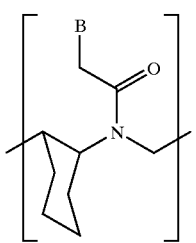

Formula IV G wherein each {BLOCK} building block can be different, and wherein z" is from 0 to 100;

G is $(CR_5R_6)_{u'}$, $C(O)NH—(CR_1R_2)_{t'}$, or $C(O)NH—(CH_2CH_2O)_{u'}—CH_2CH_2$, wherein t' is from 2 to 10;

A is, independently of any other A, a group $(CR_1R_2)_s$, wherein s is from 1 to 3;

B is, independently of any other B, either
an aromatic radical, a heteroaromatic radical, hydrogen, hydroxyl, or $C_1$–$C_{18}$-alkyl, or
a nucleobase which occurs naturally, and is customary in nucleotide chemistry, or which does not occur naturally, or its prodrug form;

D is, independently of any other D, a group $(CR_3R_4)_t$, wherein t is from 2 to 10;

E is, independently of any other E, a group $(CR_5R_6)_{u'}$, $R_5$ and $R_6$ are, independently of each other, a radical consisting of hydrogen, $C_1$–$C_6$-alkyl, or the radical of an amino acid side chain,
wherein adjacent $R_5$ and $R_6$ radicals can form a $C_5$–$C_8$-cycloalkyl ring or a spiro compound;

wherein $R_1$, $R_2$, $R_3$, $R_4$, and u' are as defined above;

and physiologically tolerated salts of the PNA derivative of Formula I,
with the provisos that at least one Y, Y', Z, or Z' radical is hydroxyl, mercapto, oxyanion, or thioate, and that at least one B radical is a nucleobase.

4. A PNA derivative as claimed in claim 3, wherein at least one Y, Y', Z, or Z' radical in Formula I is oxyanion or thioate in a pH range from 4.5 to 14.

5. A PNA derivative as claimed in claim 3, wherein n and m are 0.

6. A PNA derivative as claimed in claim 3, wherein q is 1.

7. A PNA derivative as claimed in claim 3, wherein W and W' are oxygen.

8. A PNA derivative as claimed in claim 3, wherein Y and Y' are hydroxyl or oxyanion.

9. A PNA derivative as claimed in claim 3, wherein V and V' are oxygen.

10. A PNA derivative as claimed in claim 3, wherein X and X' are, independently of each other, U—$(C_2$–$C_{22}$-alkanediyl)-U or U—$(CH_2CH_2$—$O)_{u'}$, wherein u' is from 1 to 6.

11. A PNA derivative as claimed in claim 3, wherein X, X', Z, and Z' are, independently of each other, fluorescein, rhodamine, TAMRA or cyanine dye, biotin, dabcyl, psoralen, acridine, DNP, cholesterol, vitamin E, dabcyl, edans, lexitropsin, psoralen, BODIPY, ROX, or an R6G or digoxygenin radical.

12. A PNA derivative as claimed in claim 3, wherein X, X', Z, and Z' are, independently of each other, a monophosphate, a biotin derivative, or a fluorescein derivative.

13. A PNA derivative as claimed in claim 3, wherein Z is a fluorescence label and Z' is a quencher.

14. A PNA derivative as claimed in claims 3, wherein Z is a quencher and Z' is a fluorescence label.

15. A PNA derivative as claimed in claim 3, wherein Z and Z' are, independently of each other, a $C_1$–$C_{22}$-alkyl radical, a $C_1$–$C_{22}$—U radical, hydroxy-$C_1$–$C_{18}$—U, an aminoalkyl-U radical, a group of the Formula $R_7$—$(CH_2CH_2$—$O)_m$, wherein $R_7$ is OH or $NH_2$ and m is from 1 to 6, or a mercaptoalkyl-V radical.

16. A PNA derivative as claimed in claim 3, wherein q is 0.

17. A PNA derivative as claimed in claim 16, wherein D' is acylamino.

18. A PNA derivative as claimed in claim 3, wherein D is $(CH_2)_t$.

19. A PNA derivative as claimed in claim 3, wherein A, E, and G are $CH_2$.

20. A PNA derivative as claimed in claim 3, wherein B is adenine, cytosine, 5-methylcytosine, guanine, thyinine, uracil, purine, 2,6-diaminopurine, $N^4N^4$-ethanocytosine, $N^6N^6$-ethano-2,6-diaminopurine, 5-($C_3$–$C_6$)-alkynyluracil, 5-($C_3$–$C_6$)-alkynyl-cytosine, 5-(1-propargylamino)uracil, 5-(1-propargylamino)cytosine, phenoxazine, 9-aminoethoxyphenoxazine, 5-fluorouracil or pseudoisocytosine, 5-(hydroxymethyl)uracil, 5-aminouracil, pseudouracil, dihydrouracil, 5-($C_1$–$C_6$)-alkyluracil, 5-($C_1$–$C_6$)-alkyl-cytosine, 5-($C_2$–$C_6$)-alkenylcytosine, 5-fluorocytosine, 5-chiorouracil, 5-chlorocytosine, 5-bromouracil, 5-bromocytosine, 7-deazaadenine, 7-deazaguanine, 8-azapurine, or a 7-deaza-7-substituted purine.

21. A PNA derivative as claimed in claim 3, wherein {POLY} comprises a nucleotide base sequence binds to at least one sequence of at least one tumor suppressor gene, oncogene, or telomerase, or to their mRNA transcription products.

22. A PNA derivative as claimed in claim 21, wherein the base sequence of the PNA moiety binds to the translation start of HA-ras mRNA.

23. A pharmaceutical comprising the PNA derivative as claimed in claim 1 and a physiologically acceptable carrier or excipient.

24. A pharmaceutical comprising the PNA derivative as claimed in claim 3 and a physiologically acceptable carrier or excipient.

25. A PNA derivative as claimed in claim 1, wherein the PNA derivative is a diagnostic agent.

26. The PNA derivative as claimed in claim 1, wherein the PNA derivative is an antisense agent, anti-gene agent, decoy agent, or chimeraplast agent.

27. A PNA chip comprising a PNA derivative as claimed in claim 1 and a substrate suitable for fabricating a microarray.

28. A biosensor comprising a PNA derivative as claimed in claim 1 and a substrate suitable for conducting a signal from the PNA derivative to a detection device.

29. The PNA derivative as claimed in claim 1, wherein the phosphoryl radical is a hydroxyl group or a mercapto group.

30. The PNA derivative as claimed in claim 1, wherein at least one of the phosphoryl radicals carries one or more hydroxyl or mercapto groups, which is/are deprotonatable in a pH range from 4.5 to 14.

31. The PNA derivative as claimed in claim 30, wherein said one or more hydroxyl or mercapto is/are deprotonatable in a pH from 6.5 to 12.

32. The PNA derivative as claimed in claim 30, wherein said one or more hydroxyl mercapto group is/are deprotonatable in a pH range from 6.5 to 9.

33. The PNA derivative as claimed in claim 1, wherein the phosphoryl radical is a phosphate, a phosphonate, a thiophosphate, a phosphoamidate, or a substituted phosphoryl radical, and wherein substituted phosphoryl radicals carry, where appropriate, one or more labeling groups, groups for crosslinking, groups which promote intracellular uptake, or groups which increase the binding affinity of the PNA derivative for nucleic acids.

34. The PNA derivative as claimed in claim 3, wherein u' is from 1 to 4.

35. The PNA derivative as claimed in claim 3, wherein u' is 1.

36. The PNA derivative as claimed in claim 3, wherein X, X', or both are, a bifunctional fluorescein, rhodamine, TAMRA, biotin, pyrene, dinitrophenyl, cholesteryl, acridine, adamantyl, vitamin E, cyanine dye, dabcyl, edans, lexitropsin, psoralen, BODIPY, ROX, R6G, or digoxygenin radical.

37. The PNA derivative as claimed in claim 3, wherein m' is from 2 to 10.

38. The PNA derivative as claimed in claim 3, wherein Z, Z', or both are a monofunctional or bifunctional fluorescein, rhodamine, TAMRA, biotin, pyrene, dinitrophenyl, cholesteryl, acridine, adamantyl, vitamin E, cyanine dye, dabcyl, edans, lexitropsin, psoralen, BODIPY, ROX, R6G, or digoxygenin radical.

39. The PNA derivative as claimed in claim 3, wherein $R_1$, $R_2$, or both are hydrogen.

40. The PNA derivative as claimed in claim 3, wherein $R_3$, $R_4$, or both are hydrogen.

41. The PNA derivative as claimed in claim 3, wherein n is from 0 to 3.

42. The PNA derivative as claimed in claim 3, wherein m is from 0 to 3.

43. The PNA derivative as claimed in claim 3, wherein z" is 1–20.

44. The PNA derivative as claimed in claim 3, wherein z" is 4–15.

45. The PNA derivative as claimed in claim 3, wherein t' is from 2 to 10.

46. The PNA derivative as claimed in claim 3, wherein t' is 6.

47. The PNA derivative as claimed in claim 3, wherein s is 1.

48. The PNA derivative as claimed in claim 3, wherein t is from 2 to 4.

49. The PNA derivative as claimed in claim 3, wherein t is 2.

50. The PNA derivative as claimed in claim 3, wherein $R_5$, $R_6$, or both are hydrogen.

51. The PNA derivative as claimed in claim 4, wherein at least one Y, Y', Z, or Z' radical in Formula I is oxyanion or thioate in a pH range from 6.5 to 12.

52. The PNA derivative as claimed in claim 4, wherein at least one Y, Y', Z, or Z' radical in Formula I is oxyanion or thioate in a pH range from 6.5 to 9.

53. The PNA derivative as claimed in claim 10, wherein X and X' are O—$(C_2$–$C_{22}$-alkanediyl)-O.

54. The PNA derivative as claimed in claim 10, wherein X and X' are O—$(CH_2)_{2-6}$O.

55. The PNA derivative as claimed in claim 10, wherein X and X' are U—$(CH_2CH_2$—O$)_{u'}$, wherein u' is from 1 to 6.

56. The PNA derivative as claimed in claim 10, wherein X and X' are O$(CH_2CH_2$—O$)_{u'}$, wherein u' is from 1 to 6.

57. The PNA derivative as claimed in claim 15, wherein Z and Z' are, independently of each other, a $C_1$–$C_{22}$-alkoxy radical.

58. The PNA derivative as claimed in claim 15, wherein Z and Z' are, independently of each other, $C_{16}$-alkoxy.

59. The PNA derivative as claimed in claim 15, wherein Z and Z' are, independently of each other, hydroxy-$C_1$–$C_{18}$—O.

60. The PNA derivative as claimed in claim 15, wherein Z and Z' are, independently of each other, HO—$(CH_2)_{3-12}$O.

61. The PNA derivative as claimed in claim 15, wherein Z and Z' are, independently of each other, an aminoalkoxy radical.

62. The PNA derivative as claimed in claim 15, wherein Z and Z' are, independently of each other, 6-aminohexoxy or 5-aminopentoxy.

63. The PNA derivative as claimed in claim 15, wherein Z and Z' are, independently of each other, HO$(CH_2CH_2$—O$)_2$.

64. The PNA derivative as claimed in claim 15, wherein Z and Z' are, independently of each other, HO$(CH_2CH_2$—O$)_6$.

65. The PNA derivative as claimed in claim 15, wherein Z and Z' are, independently of each other, $H_2N$—$(CH_2CH_2$—O$)_2$.

66. The PNA derivative as claimed in claim 15, wherein Z and Z' are, independently of each other, a mercaptoalkoxy radical.

67. The PNA derivative as claimed in claim 15, wherein Z and Z' are, independently of each other, 6-mercaptohexyloxy.

68. The PNA derivative as claimed in claim 17, wherein D' is acetylamino.

69. The PNA derivative as claimed in claim 15, wherein D is $(CH_2)_2$.

* * * * *